US012576004B2

(12) United States Patent
Hong et al.

(10) Patent No.: US 12,576,004 B2
(45) Date of Patent: Mar. 17, 2026

(54) MASK

(71) Applicant: LG INNOTEK CO., LTD., Seoul (KR)

(72) Inventors: Beom Sun Hong, Seoul (KR); Hae Rok Son, Seoul (KR); Gyu Lin Lee, Seoul (KR); Min Seok Oh, Seoul (KR); Mi Sun Lee, Seoul (KR)

(73) Assignee: LG INNOTEK CO., LTD., Seoul (KR)

( * ) Notice: Subject to any disclaimer, the term of this patent is extended or adjusted under 35 U.S.C. 154(b) by 1036 days.

(21) Appl. No.: 17/761,245

(22) PCT Filed: Sep. 1, 2020

(86) PCT No.: PCT/KR2020/011699
§ 371 (c)(1),
(2) Date: Mar. 17, 2022

(87) PCT Pub. No.: WO2021/054649
PCT Pub. Date: Mar. 25, 2021

(65) Prior Publication Data
US 2022/0362100 A1      Nov. 17, 2022

(30) Foreign Application Priority Data

Sep. 17, 2019   (KR) ........................ 10-2019-0114056
Dec. 6, 2019   (KR) ........................ 10-2019-0161440

(51) Int. Cl.
*A61H 23/00*      (2006.01)
*A61H 23/02*      (2006.01)
*A61N 7/00*      (2006.01)
(52) U.S. Cl.
CPC ... *A61H 23/0245* (2013.01); *A61H 2205/022* (2013.01); *A61N 2007/0034* (2013.01)

(58) Field of Classification Search
CPC ........ A61H 2205/022; A61H 2205/023; A61H 2205/025; A61H 2205/024; A61H 23/0245; A61N 2007/0034; A61N 2007/0078; A61M 37/0092; A61M 2210/0606
See application file for complete search history.

(56) References Cited

U.S. PATENT DOCUMENTS 5,493,541 A * 2/1996 Snyder ................... H04R 17/00
                                                        310/365
8,884,497 B2   11/2014 Takahashi et al.
(Continued)

FOREIGN PATENT DOCUMENTS

CN        102405591 A      4/2012
CN        105722548 A      6/2016
(Continued)

OTHER PUBLICATIONS

International Search Report (PCT/ISA/210) issued in PCT/KR2020/011699 mailed on Dec. 11, 2020.

*Primary Examiner* — William R Carpenter
(74) *Attorney, Agent, or Firm* — Birch, Stewart, Kolasch & Birch, LLP

(57) ABSTRACT

A mask according to an embodiment comprises: a body having a shape corresponding to a user's face; a first recess disposed on one surface of the body, opposite to the user's face; and a piezoelectric part disposed in the first recess, wherein the first recess has a shape recessed outward from the one surface of the body and is disposed in a region corresponding to at least one of the user's brow region and eye rim regions, and the piezoelectric unit protrudes beyond the one surface toward the user.

16 Claims, 22 Drawing Sheets

(56)            References Cited

U.S. PATENT DOCUMENTS

| | | | |
|---|---|---|---|
| 9,634,428 | B2 | 4/2017 | DiFonzo et al. |
| 11,691,002 | B2 | 7/2023 | Yamazaki |
| 2008/0139943 | A1 | 6/2008 | Deng et al. |
| 2012/0007477 | A1 | 1/2012 | Takahashi et al. |
| 2014/0276248 | A1 * | 9/2014 | Hall ..................... A61N 1/30 |
| | | | 604/20 |
| 2016/0303360 | A1 | 10/2016 | Mulvihill et al. |
| 2018/0360420 | A1 | 12/2018 | Vortman et al. |
| 2020/0353244 | A1 | 11/2020 | Yamazaki |

FOREIGN PATENT DOCUMENTS

| | | | | |
|---|---|---|---|---|
| CN | 109865199 | A | 6/2019 | |
| DE | 102017117053 | A1 * | 10/2018 | ............. A61B 5/398 |
| JP | 2000-317821 | A | 11/2000 | |
| KR | 20-0279590 | Y1 | 6/2002 | |
| KR | 10-0851060 | B1 | 8/2008 | |
| KR | 10-1013036 | B1 | 2/2011 | |
| KR | 10-2011-0074243 | A | 6/2011 | |
| KR | 10-1093103 | B1 | 12/2011 | |
| KR | 10-1170040 | B1 | 8/2012 | |
| KR | 20120122125 | A * | 11/2012 | ........ A61M 37/0092 |
| KR | 101214552 | B1 * | 12/2012 | ............. A61H 39/00 |
| KR | 10-2015-0120114 | A | 10/2015 | |
| KR | 10-2016-0035202 | A | 3/2016 | |
| KR | 101637343 | B1 * | 7/2016 | .......... A61N 5/0625 |
| KR | 20-2017-0000109 | U | 1/2017 | |
| KR | 10-1892555 | B1 | 8/2018 | |
| KR | 10-2019-0008451 | A | 1/2019 | |
| WO | WO 2015/076467 | A1 | 5/2015 | |
| WO | WO 2015/188811 | A1 | 12/2015 | |

* cited by examiner

[Fig. 1]
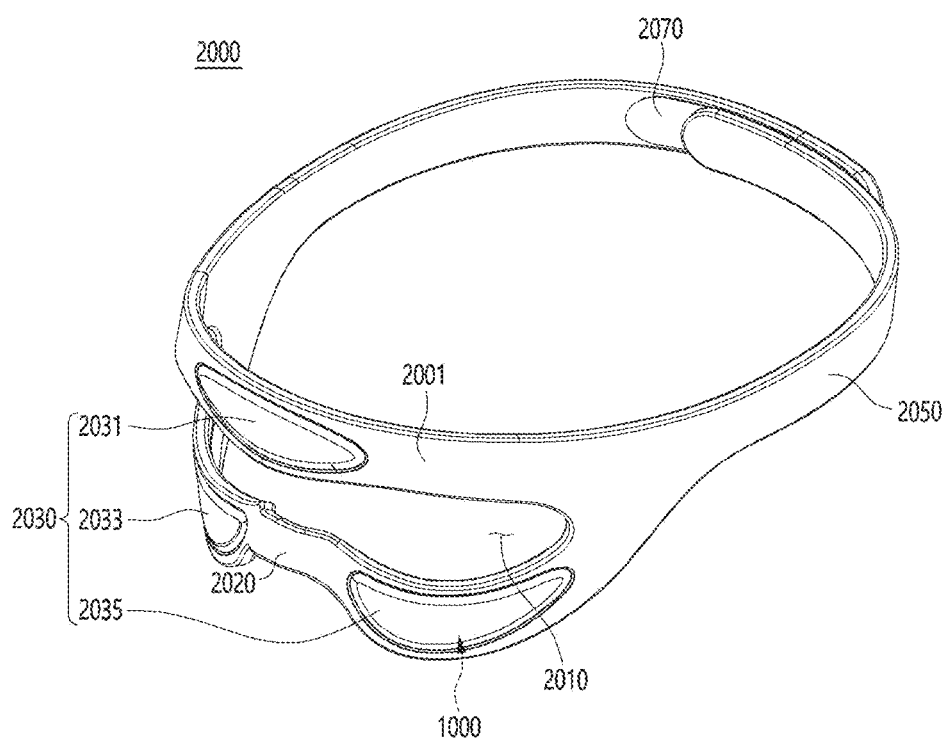

【Fig. 2】
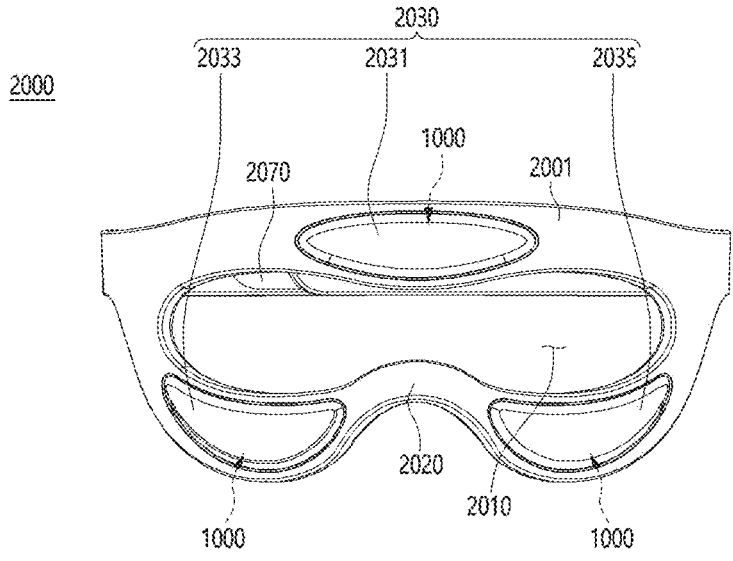
【Fig. 3】
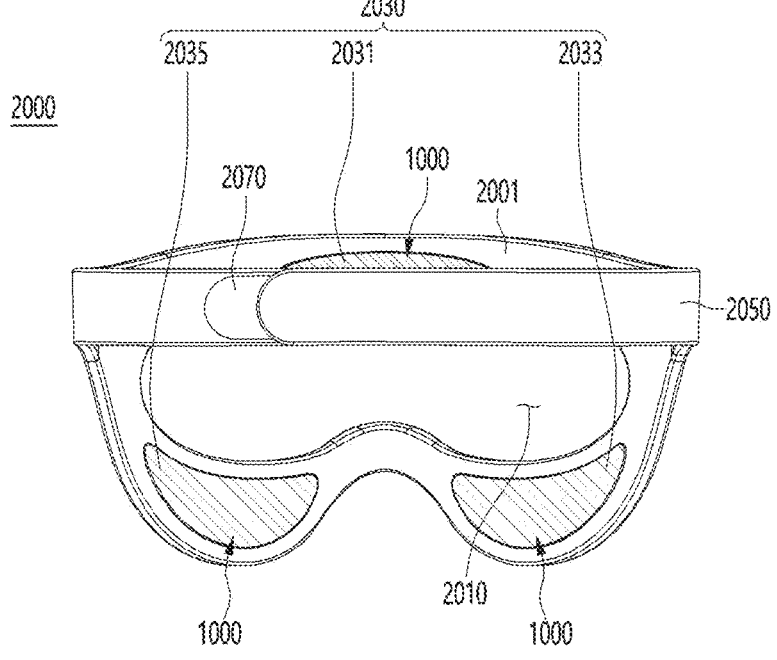

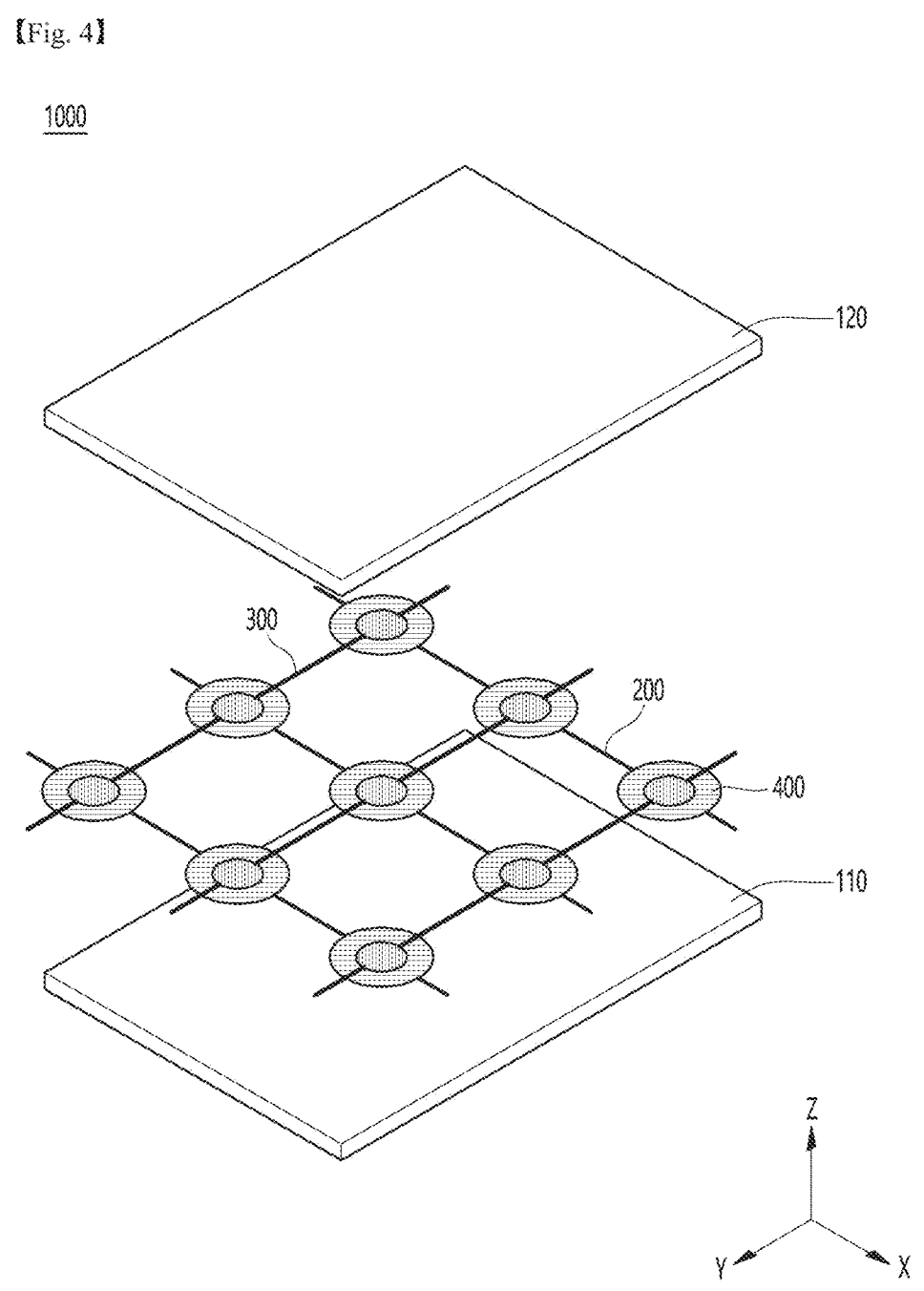

[Fig. 5]
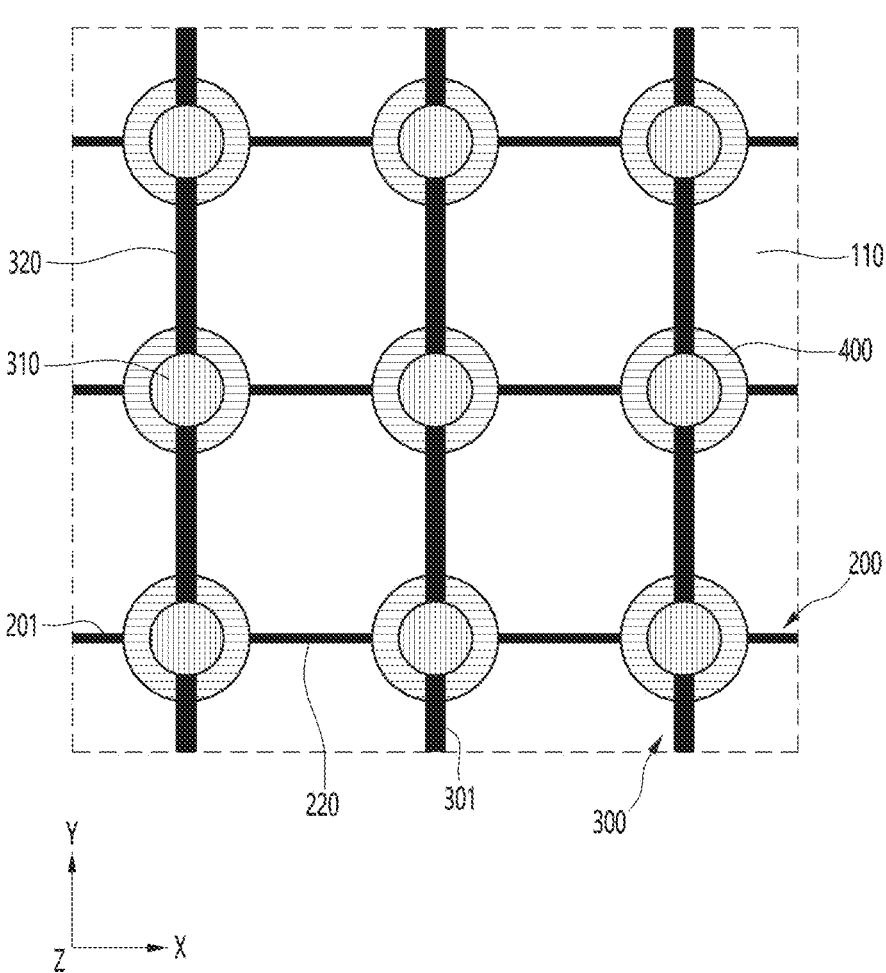

[Fig. 6]
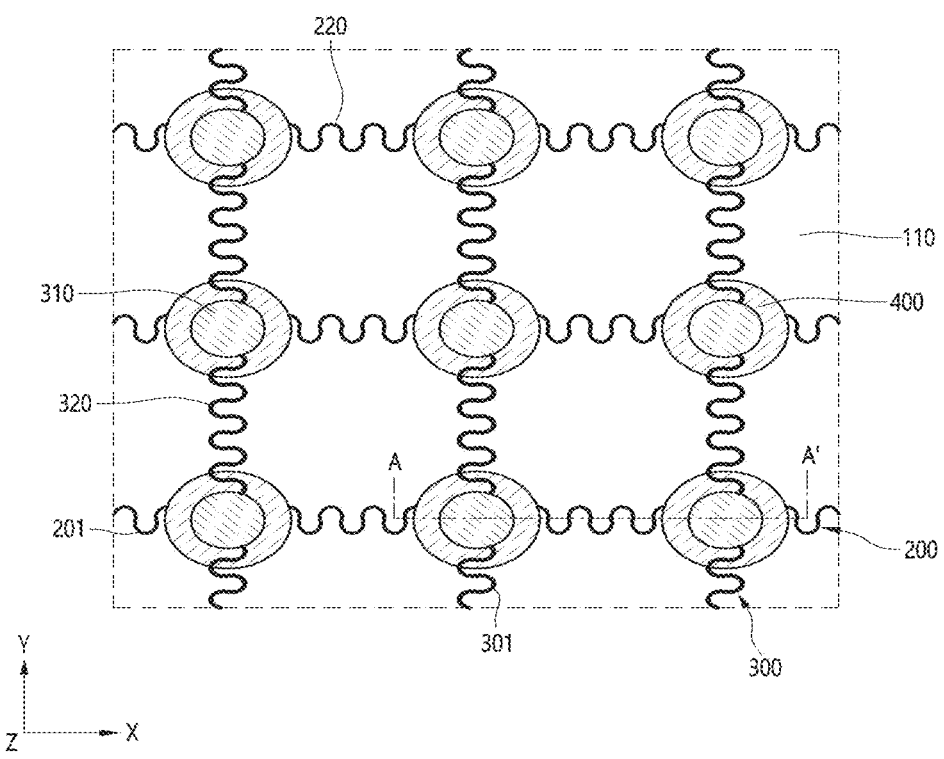

【Fig. 7】
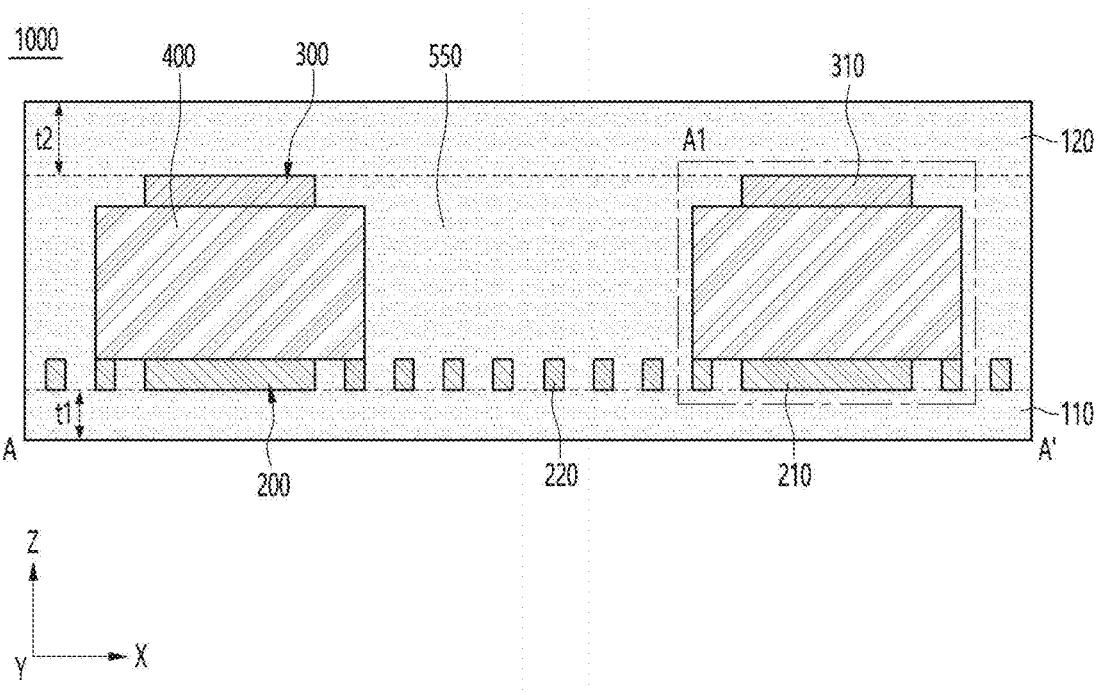

【Fig. 8】
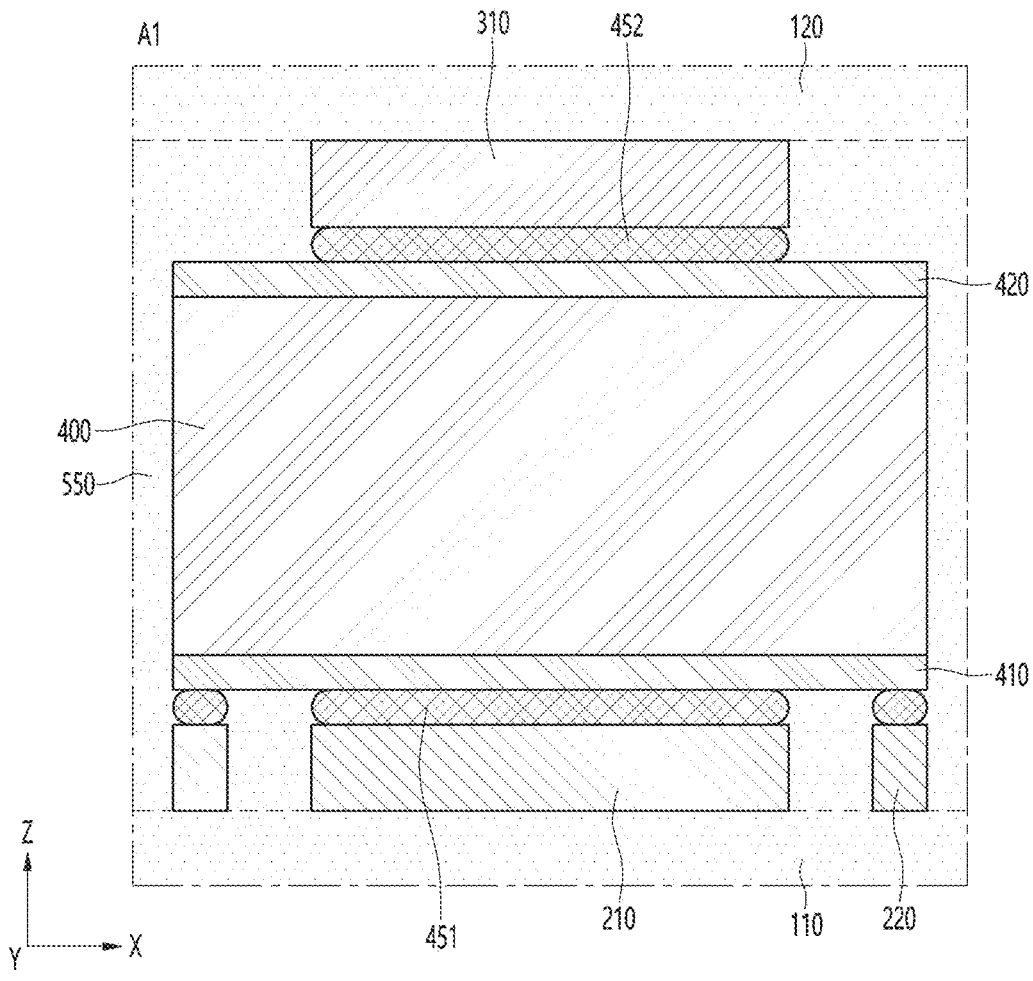

【Fig. 9】
1000
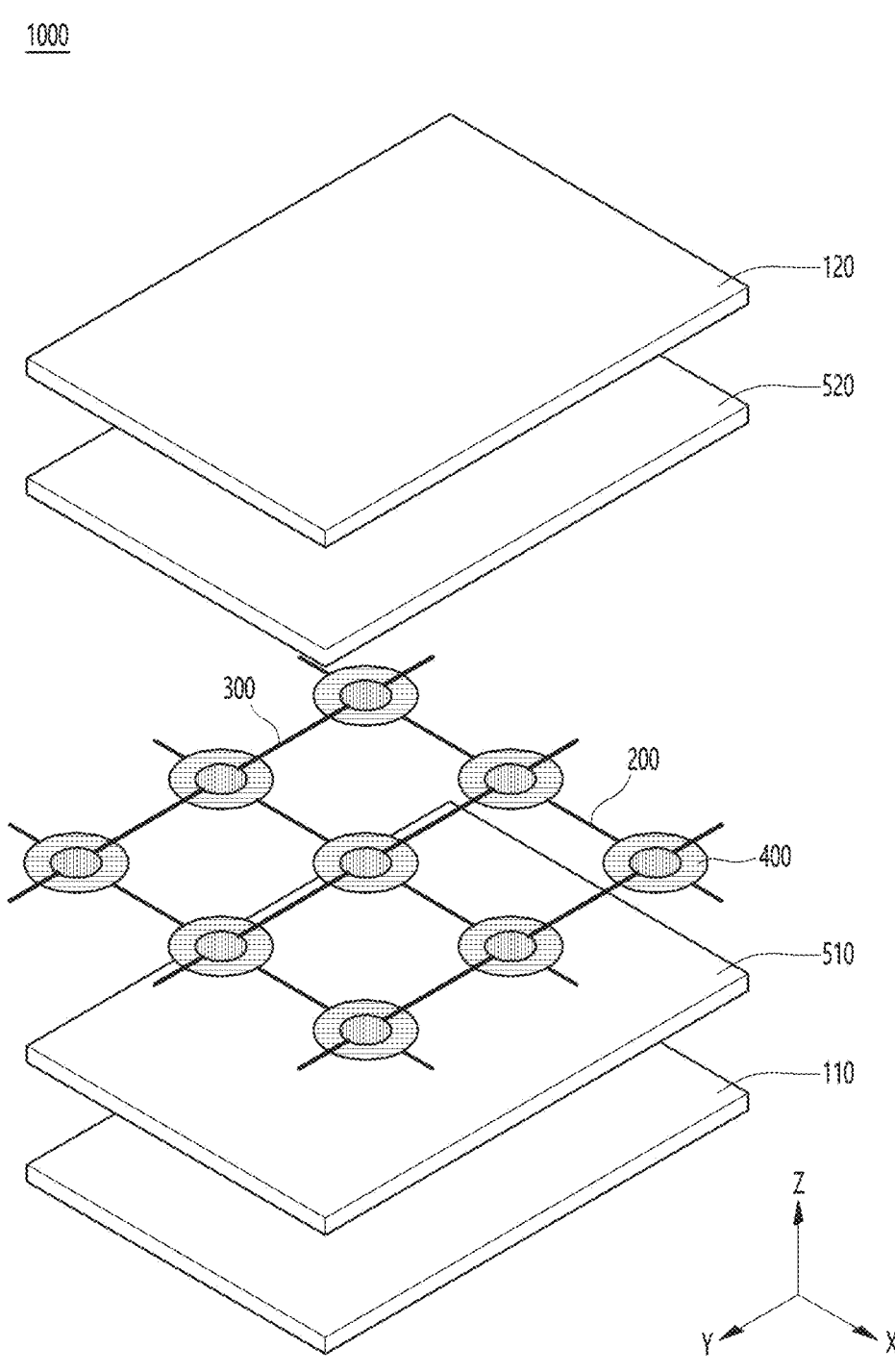

[Fig. 10]
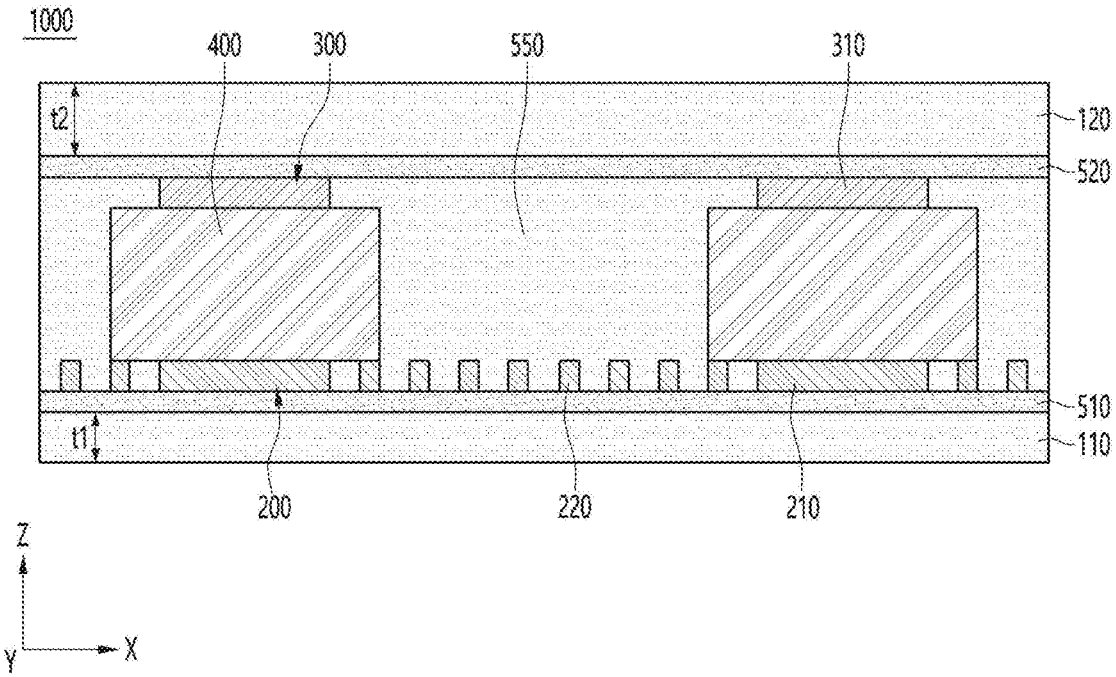

【Fig. 11】
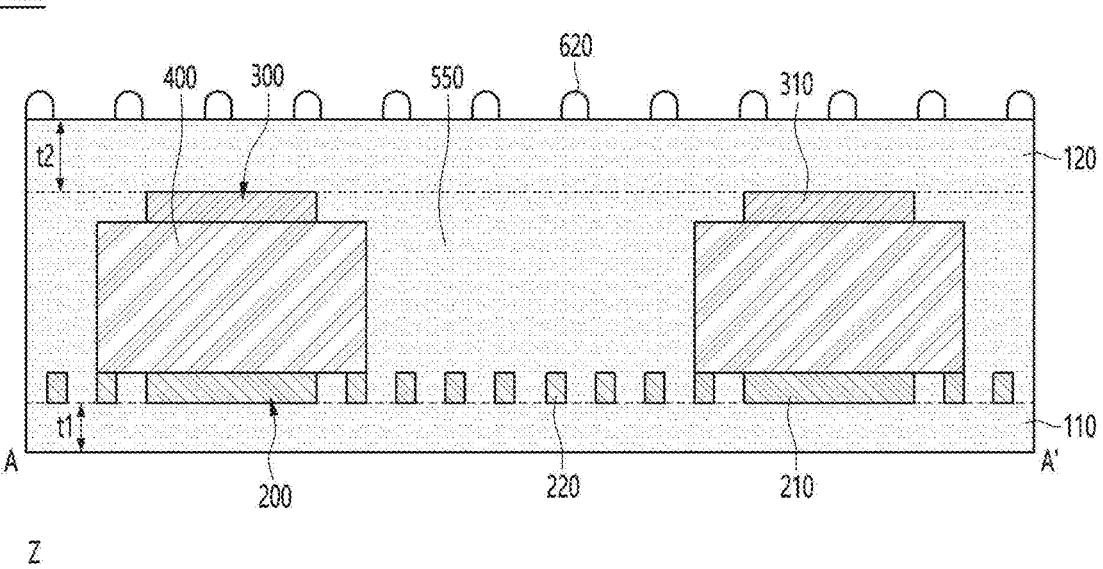
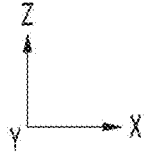

[Fig. 12]
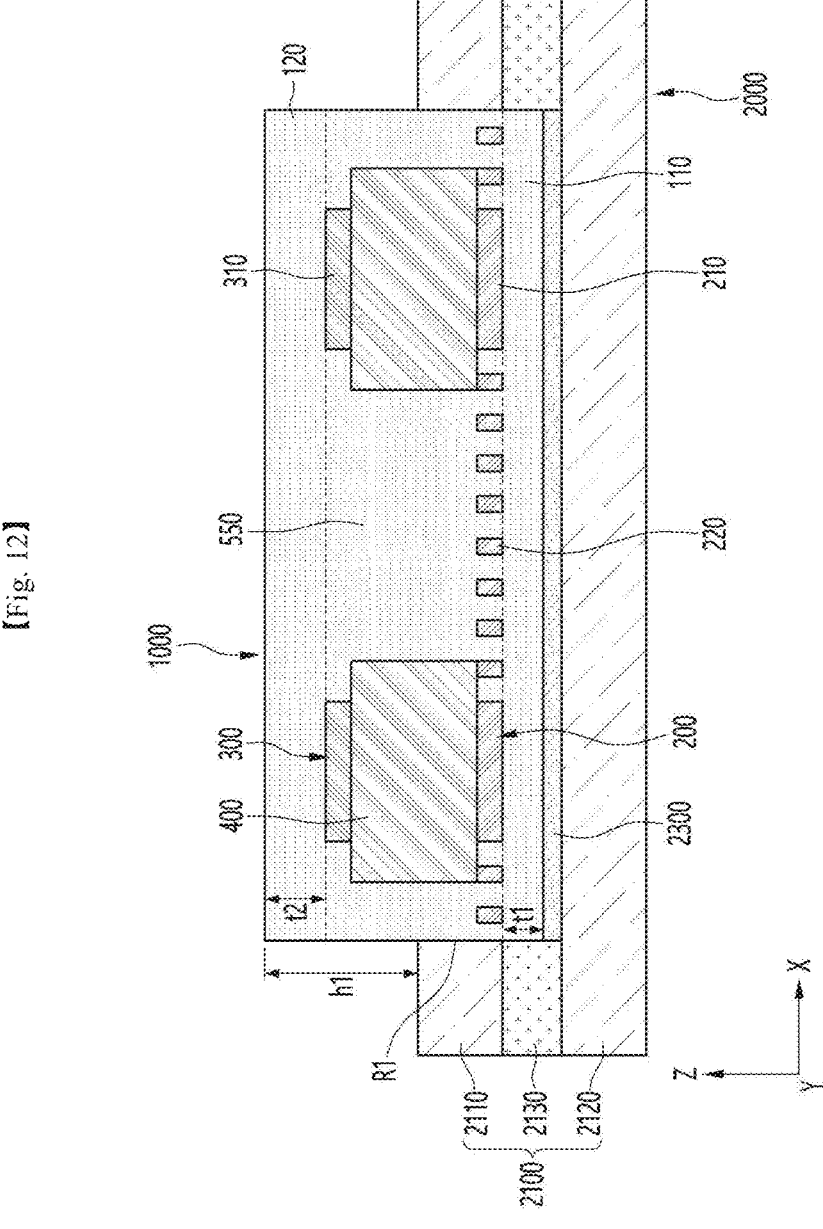

[Fig. 13]
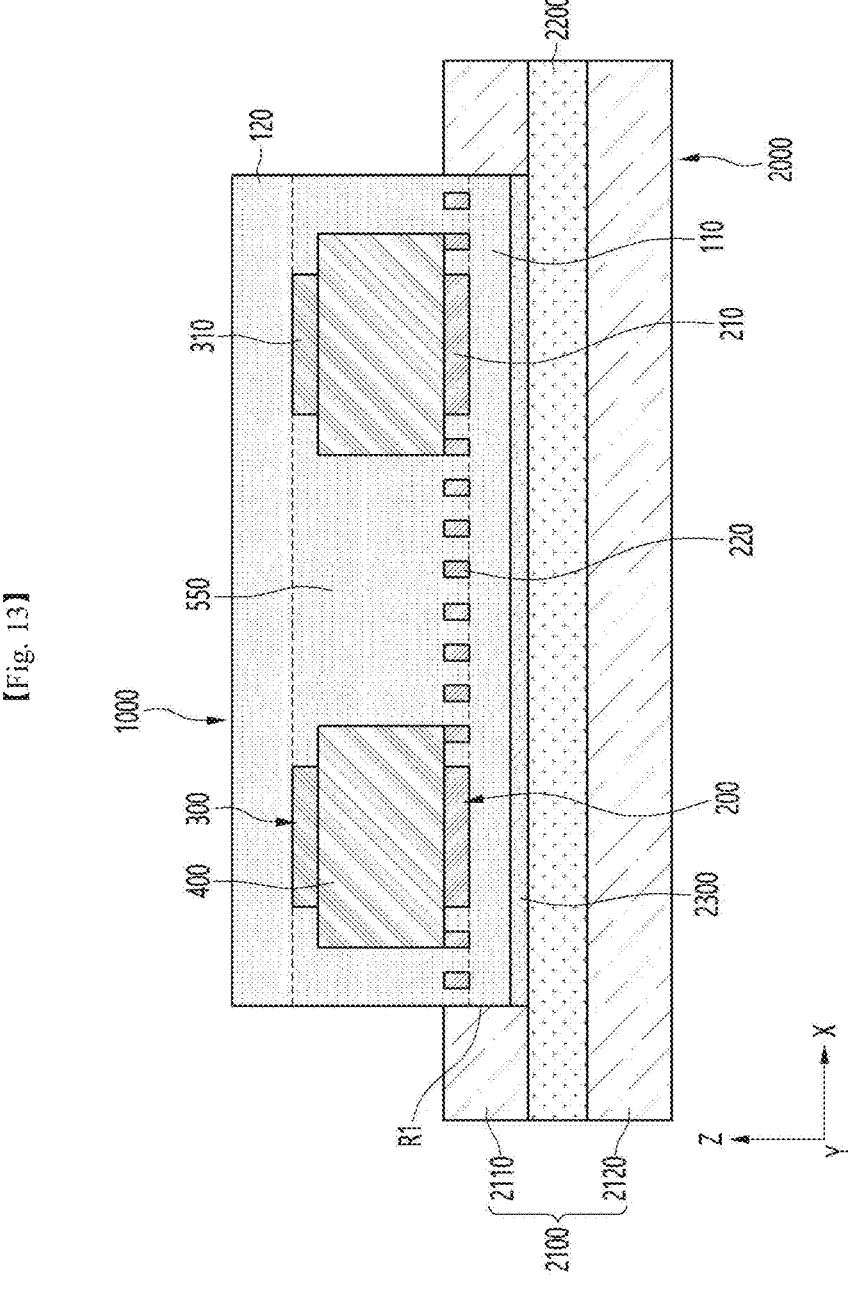

[Fig. 14]
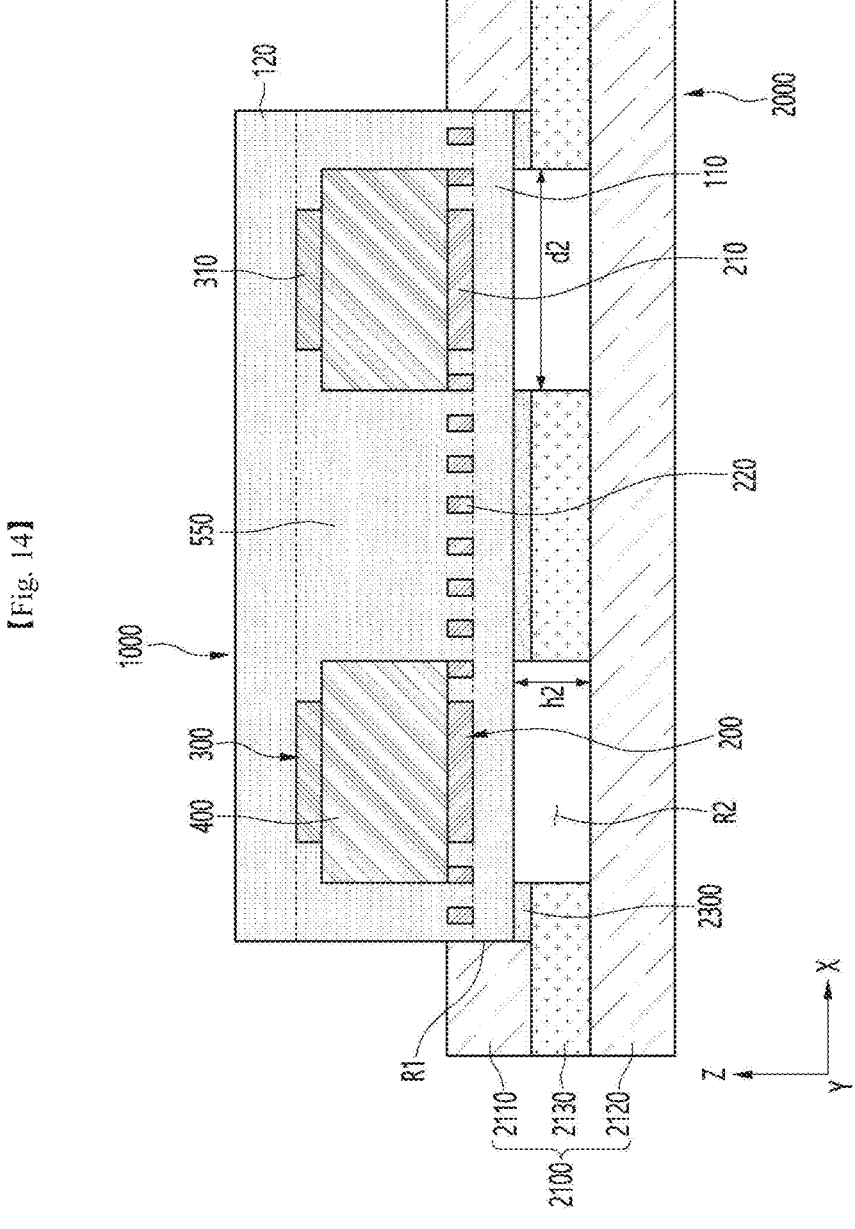

[Fig. 15]
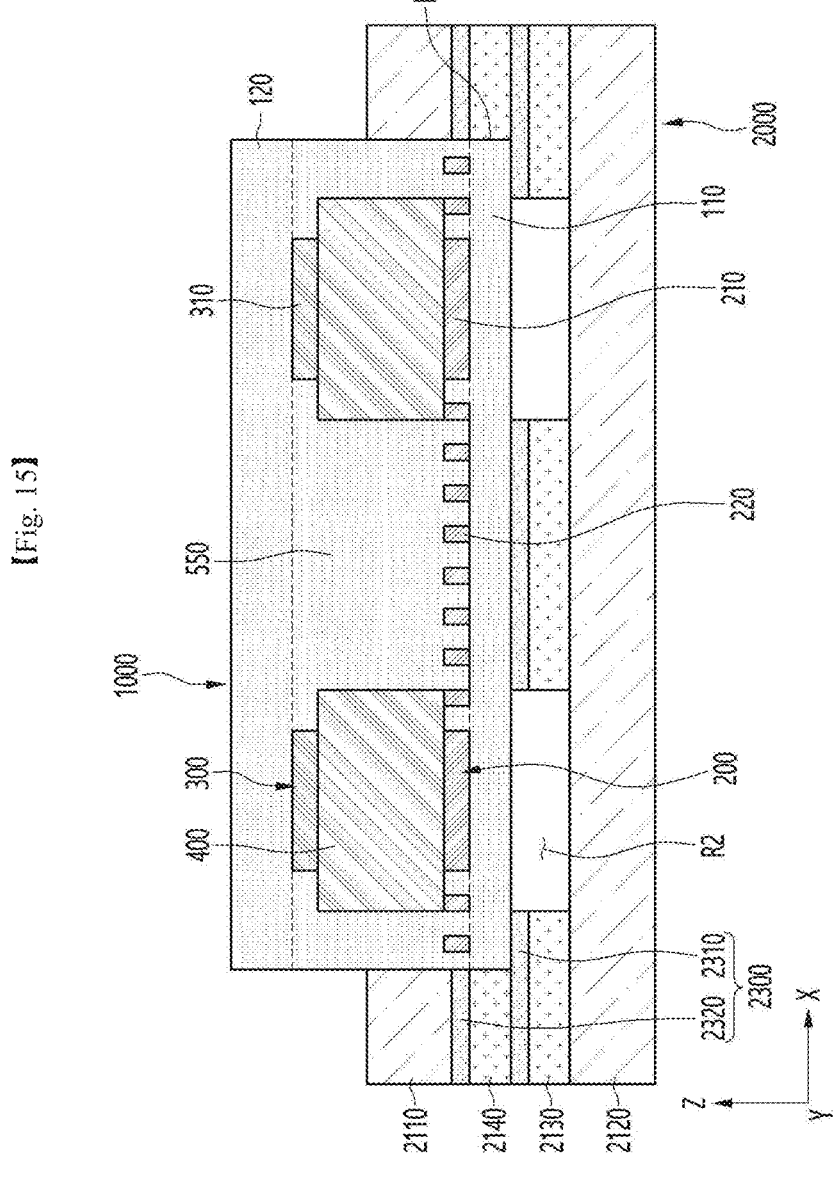

【Fig. 16】
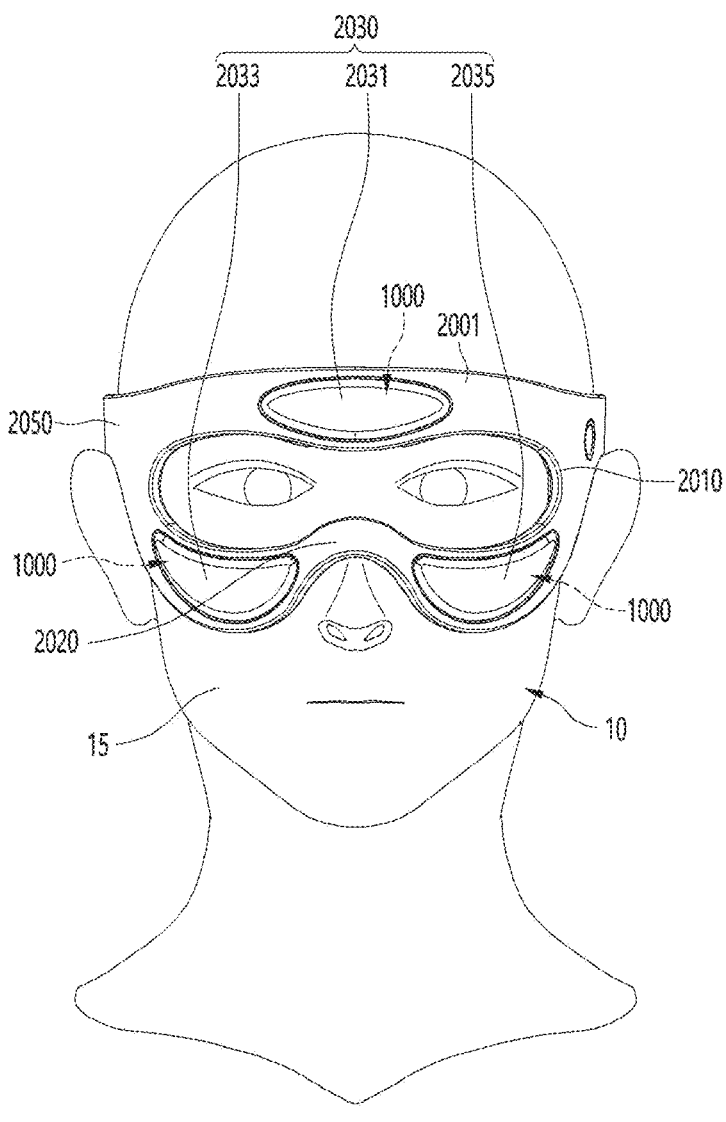

[Fig. 17]
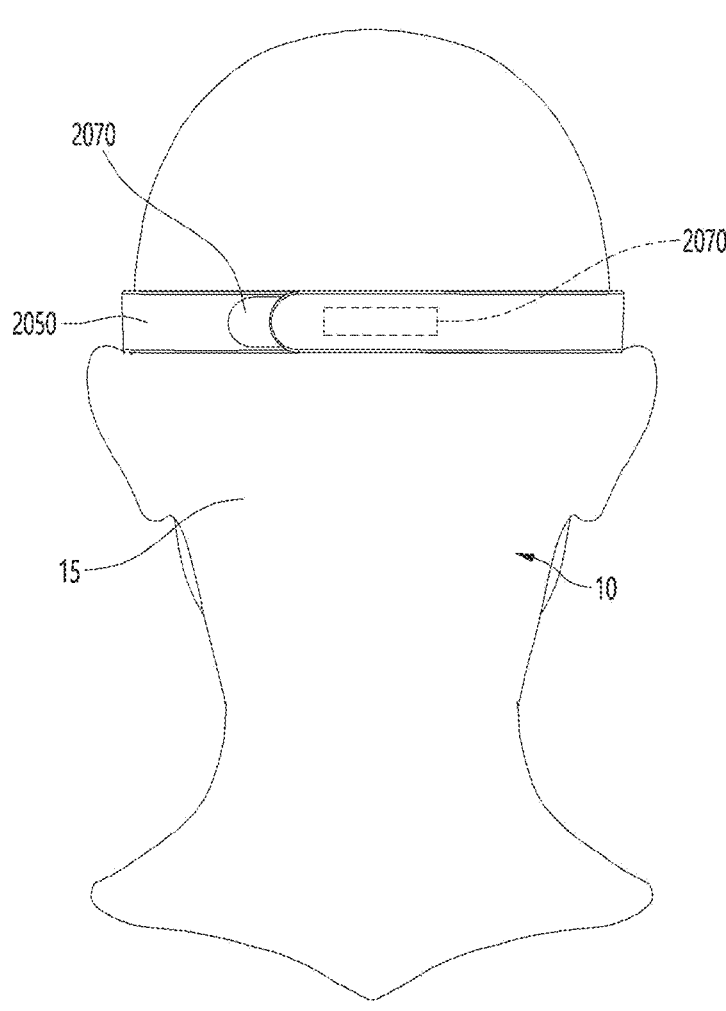

[Fig. 18]
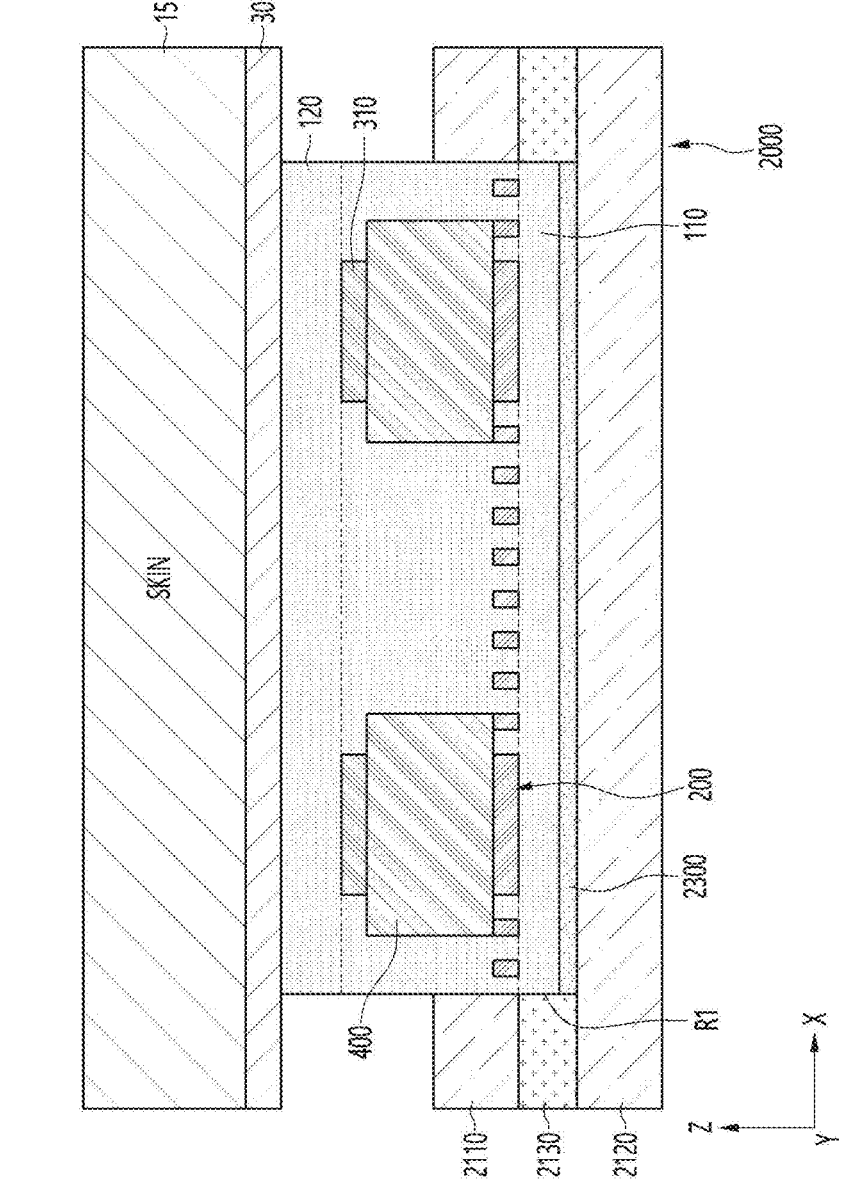

[Fig. 19]
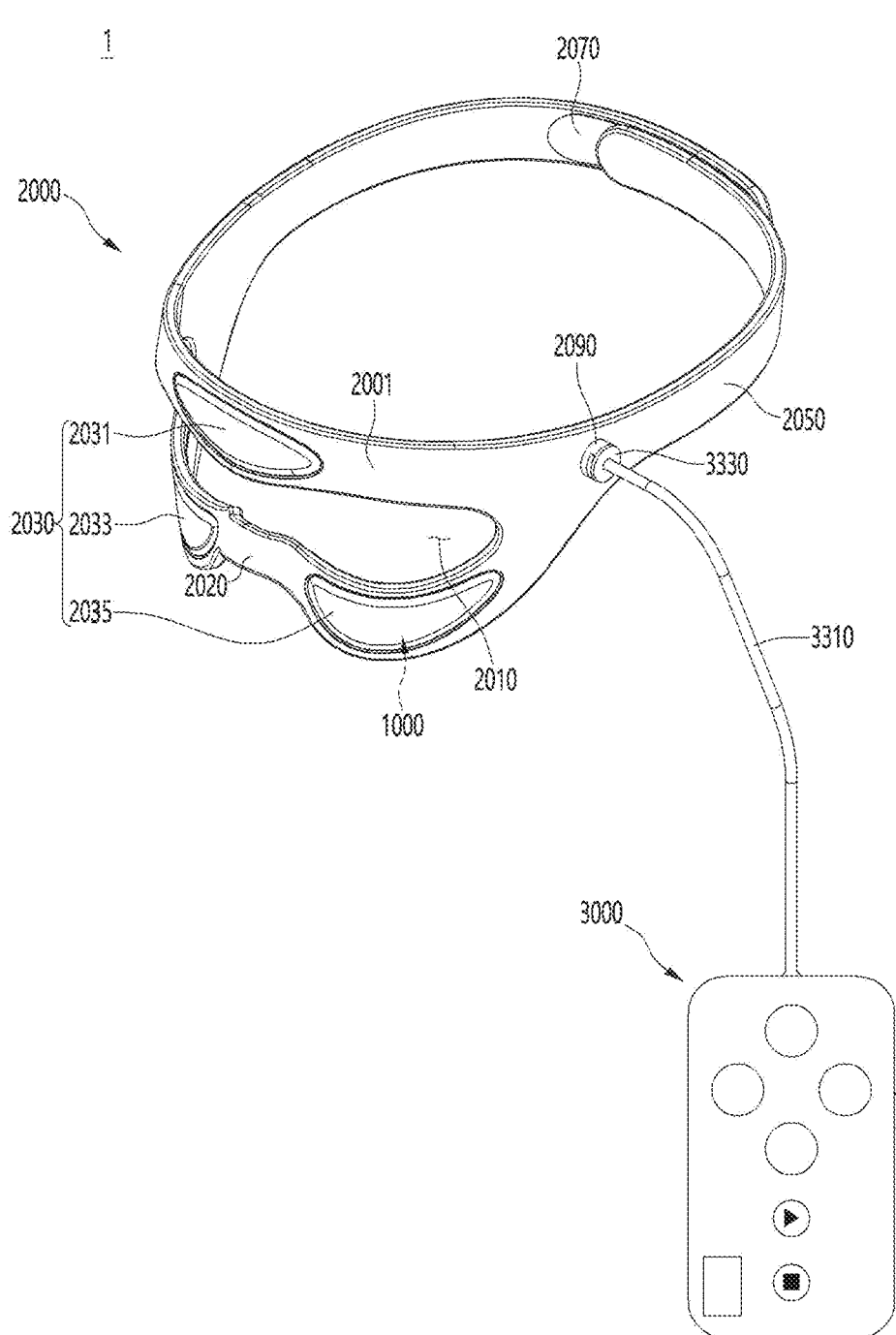

[Fig. 20]
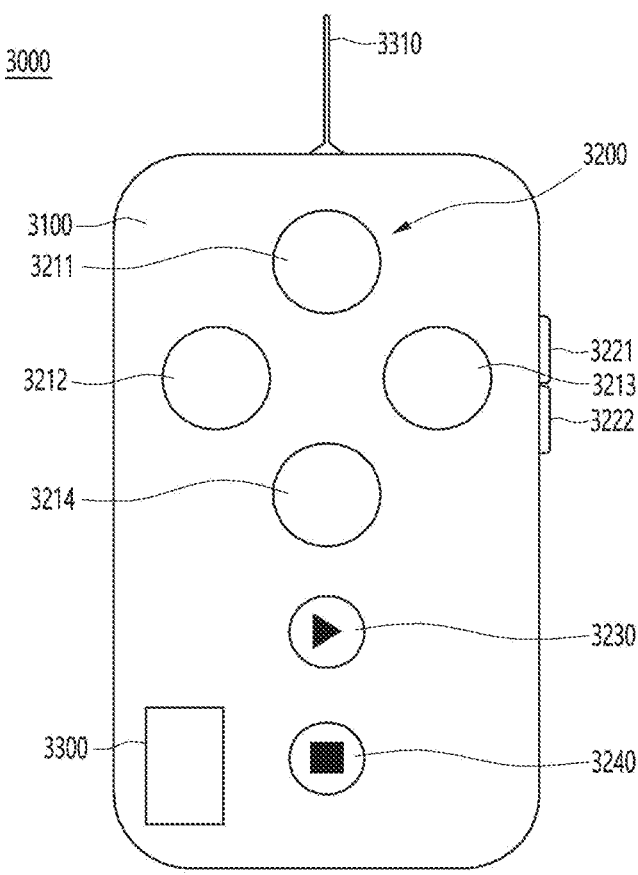

[Fig. 21]
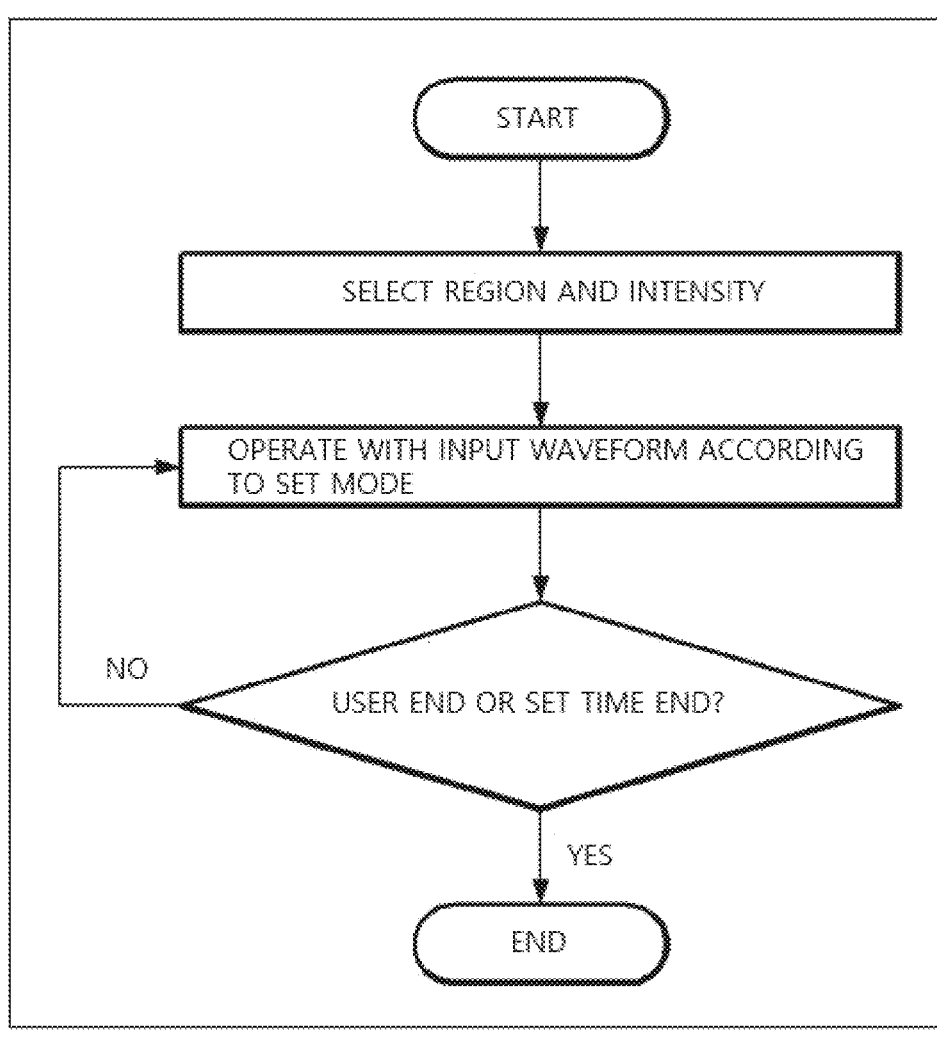

【Fig. 22】
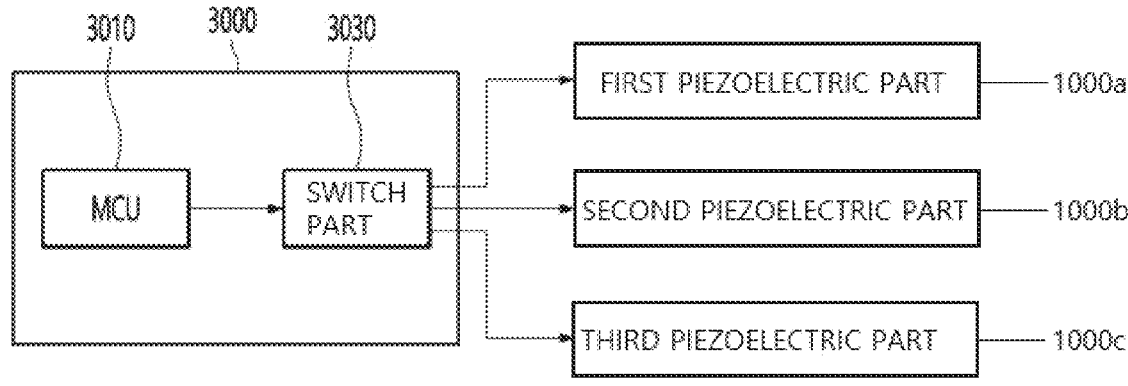
【Fig. 23】
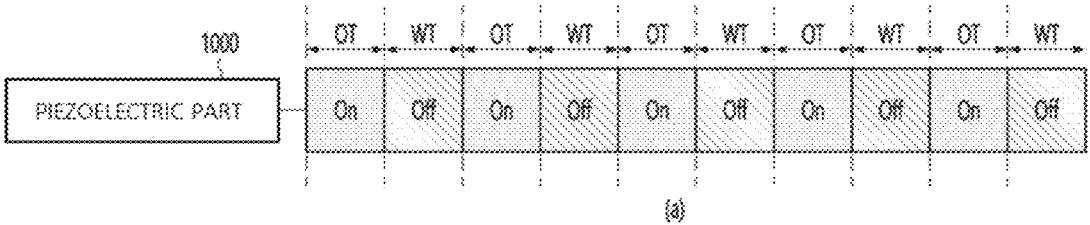
(a)
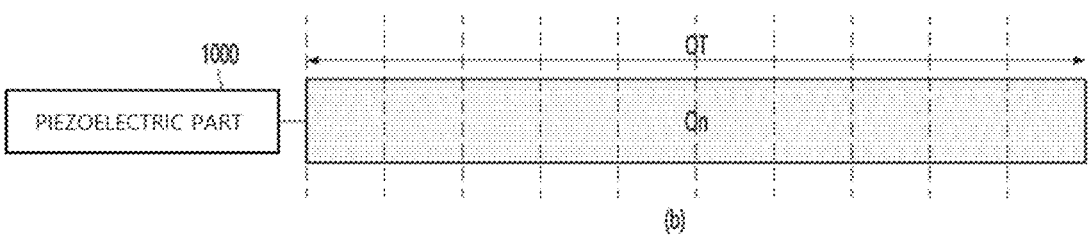
(b)

【Fig. 24】
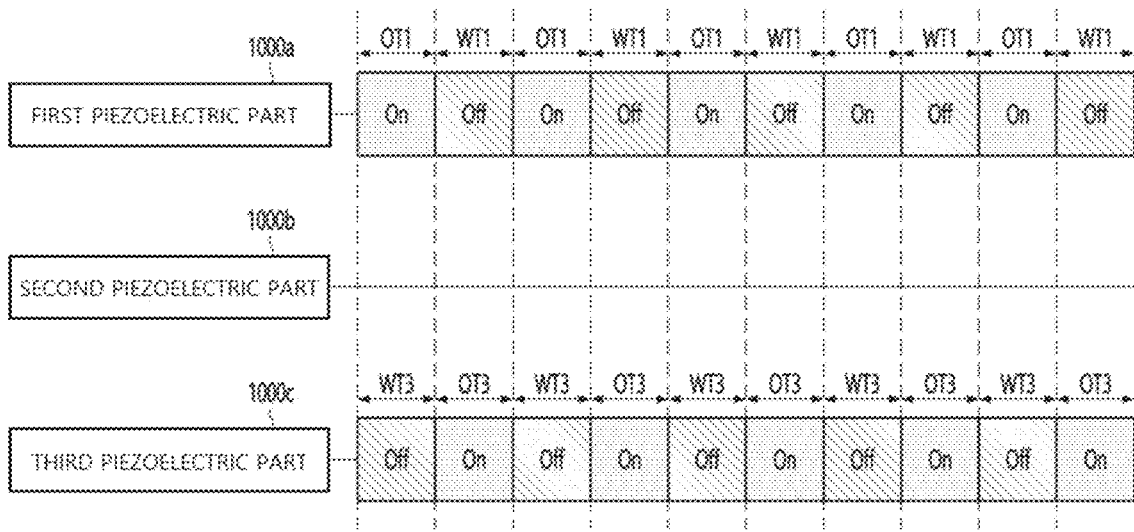
【Fig. 25】
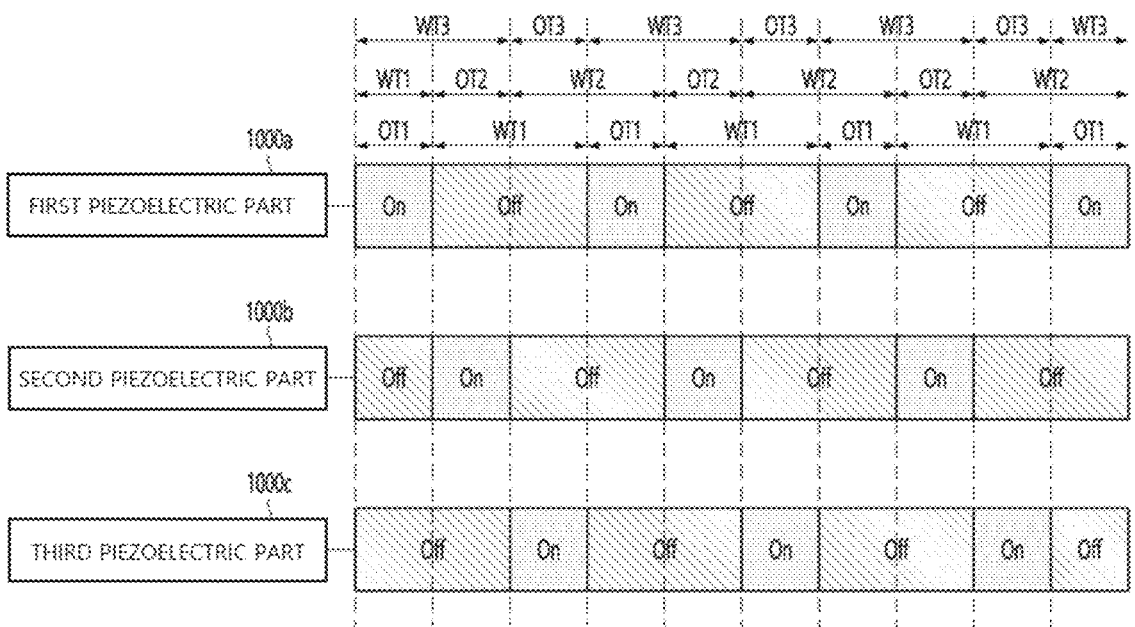

MASK

CROSS REFERENCE TO RELATED APPLICATIONS

This application is the National Phase of PCT International Application No. PCT/KR2020/011699, filed on Sep. 1, 2020, which claims priority under 35 U.S.C. 119(a) to Patent Application Nos. 10-2019-0114056, filed in the Republic of Korea on Sep. 17, 2019 and 10-2019-0161440, filed in the Republic of Korea on Dec. 6, 2019, all of which are hereby expressly incorporated by reference into the present application.

TECHNICAL FIELD

An embodiment relates to a mask.

BACKGROUND ART

Human skin may be damaged or contaminated depending on external factors such as environmental pollution, ultraviolet rays, stress, and the like, and wrinkles may occur due to internal factors such as aging, hormonal changes, and the like. Recently, as interest in the skin has increased, various devices for skin treatment, beauty, and anti-aging have been developed.

In detail, a device has been developed, which is capable of applying thermal energy to the skin, for example, a device capable of improving skin elasticity by applying infrared energy. In addition, a device using sound waves or light rays has been developed in order to effectively inject cosmetics or drugs into the skin. For example, a device has been developed, which is capable of forming a path through which cosmetics or drugs are injected into the skin using sonophoresis and laserporation. In addition, a device using electric propulsion force has been developed in order to effectively inject cosmetics or drugs into the skin. For example, a device has been developed, which is capable of effectively injecting ionic substances contained in cosmetics or drugs into the skin using iontophoresis, electroporation, and electroosmosis. That is, various devices have been developed, which is capable of caring or treating a user's skin by providing light energy, microcurrent, vibration, or the like to the skin.

In general, the above-described devices may be provided in a form of a patch detachable to the skin, and the devices are attached to a specific skin region to care or treat the skin of the attached region. In addition, the above-described devices are provided in a form of a mask pack disposed to cover the entire user's face to care or treat the facial skin.

However, since the devices are formed to have a predetermined thickness, it may be difficult to effectively adhere to the user's skin.

In addition, the devices are difficult to effectively adhere to the user's skin in curved regions such as both cheeks, nose, and the like. In detail, it may be difficult to effectively adhere to the user's skin due to materials and variable characteristics of the device. Accordingly, the device may be operated in a state in which the device is not completely adhered to the user's skin, and the device may be separated from the user's skin due to the user's movement or vibration of the device during the operation thereof. Accordingly, since ultrasonic energy is not provided to the user's skin, a care or treatment effect using the device may be insignificant.

In addition, there is a problem that an internal electric wiring is damaged due to the deformation of the device that occurs while the device is adhered to the user's skin. In particular, there is a problem that an electric wiring of the device in a region corresponding to a relatively curved skin is disconnected due to deformation of the device that occurs when the device is worn.

In addition, there is a problem that the device is deformed while the device is adhered to the user's skin. Accordingly, there is a problem that impedance characteristics of ultrasonic waves generated from a piezoelectric element of the device are deteriorated. Accordingly, the device has a problem that it is difficult to effectively transmit ultrasonic energy to the user's skin and it is difficult to evenly transmit the ultrasonic energy to the entire skin region.

Therefore, a new mask capable of solving the above-described problem is required.

DISCLOSURE

Technical Problem

An embodiment is to provide a mask that has variability and improved reliability.

In addition, an embodiment is to provide a mask capable of effectively adhering to a user's skin.

In addition, an embodiment is to provide a mask capable of providing uniform ultrasonic energy to a user's skin.

In addition, an embodiment is to provide a mask capable of effectively caring or treating the user's skin in a short time.

Technical Solution

A mask according to an embodiment includes a body having a shape corresponding to a user's face, a first recess disposed on one surface of the body facing the user's face, and a piezoelectric part disposed in the first recess, wherein the first recess has a concave shape from one surface of the body in an outward direction and is disposed in a region corresponding to at least one of the user's brow region and eye rim regions, and the piezoelectric part protrudes further toward the user than one surface of the body.

In addition, a mask according to an embodiment includes a body having a second support member, a third support member on the second support member, and a first support member on the third support member, a first recess disposed on the first support member, and a piezoelectric part disposed in the first recess, wherein the first recess has a concave shape from the first support member toward the second support member, and the third support member includes a material different from the first and second support members, wherein the piezoelectric part includes a first base layer disposed on the second support member, a first wiring disposed on the first base layer, a plurality of piezoelectric elements disposed on the first wiring, a second wiring disposed on the plurality of piezoelectric elements, a second base layer disposed on the second wiring, and a protective layer disposed between the first and second base layers and surrounding the first wiring, the second wiring, and the plurality of piezoelectric elements, wherein an upper surface of the second base layer is disposed above an upper surface of the first support member.

Advantageous Effects

A mask according to an embodiment includes an elastic material and may be elastically deformed depending on a shape of a user's skin. Accordingly, when the user wears the mask, the mask may be deformed into a shape corresponding to the user's skin, so that the mask may be effectively adhered to the skin of the user.

In addition, the mask according to the embodiment may include a piezoelectric part, and the piezoelectric parts may be disposed in a position corresponding to a region where wrinkles are relatively easy to occur, a region where a stratum corneum is easily formed, and a region where effective supply of cosmetics or drugs is required of the user's skin. As an example, the piezoelectric part may be disposed in a region corresponding to the user's brow region and both eye rim regions to provide ultrasonic energy to the region. Accordingly, the mask may crack the stratum corneum of the region to form fine perforations and effectively provide drugs or cosmetics between the piezoelectric part and the skin into the skin.

In addition, the piezoelectric part may include a plurality of piezoelectric elements and may be elastically deformed depending on the shape of the user's skin. Accordingly, the piezoelectric part may be effectively adhered to the user's skin to generate uniform ultrasonic energy on the user's skin. In particular, the plurality of piezoelectric elements may be disposed at different intervals from each other depending on a face shape of the user. For example, the piezoelectric elements disposed in a relatively curved region such as cheekbones, cheeks, and the like and a planar region such as brow of surface regions of the user's skin may be disposed at different intervals from each other. Accordingly, the mask according to the embodiment may provide uniform ultrasound energy to various skin shapes without being limited to the skin type.

DESCRIPTION OF DRAWINGS

FIG. 1 is a perspective view of a mask according to an embodiment.

FIG. 2 is a front view of the mask according to the embodiment.

FIG. 3 is a rear view of the mask according to the embodiment

FIG. 4 is an exploded perspective view of a piezoelectric part according to an embodiment.

FIG. 5 is a top view of the piezoelectric part according to the embodiment.

FIG. 6 is another top view of the piezoelectric part according to the embodiment.

FIG. 7 is a cross-sectional view taken along line A-A' of FIG. 6.

FIG. 8 is an enlarged view of region A1 in FIG. 7.

FIG. 9 is another exploded perspective view of the piezoelectric part according to the embodiment.

FIG. 10 is a cross-sectional view of the piezoelectric part of FIG. 9.

FIG. 11 is a cross-sectional view showing an example in which a protrusion is provided on the piezoelectric part according to the embodiment.

FIG. 12 is a cross-sectional view of an arrangement relationship between a body and a piezoelectric part according to an embodiment.

FIGS. 13 to 15 are other cross-sectional views of the arrangement relationship between the body and the piezoelectric part according to the embodiment.

FIG. 16 is a front view of a user wearing a mask according to an embodiment.

FIG. 17 is a rear view of the user wearing the mask according to the embodiment.

FIG. 18 is a view showing an arrangement relationship between a mask and a skin according to an embodiment.

FIG. 19 is a perspective view of a skin care device according to an embodiment.

FIG. 20 is a front view of a controller according to an embodiment.

FIG. 21 is a flowchart showing an operation of the skin care device according to the embodiment.

FIG. 22 is a block diagram showing a configuration of the skin care device according to the embodiment.

FIGS. 23 to 25 are diagrams showing a method of operating first to third piezoelectric parts according to an embodiment.

MODES OF THE INVENTION

Hereinafter, embodiments of the present invention will be described in detail with reference to the accompanying drawings.

However, the spirit and scope of the present invention is not limited to a part of the embodiments described, and may be implemented in various other forms, and within the spirit and scope of the present invention, one or more of the elements of the embodiments may be selectively combined and replaced.

In addition, unless expressly otherwise defined and described, the terms used in the embodiments of the present invention (including technical and scientific terms may be construed the same meaning as commonly understood by one of ordinary skill in the art to which this invention belongs, and the terms such as those defined in commonly used dictionaries may be interpreted as having a meaning that is consistent with their meaning in the context of the relevant art.

In addition, the terms used in the embodiments of the present invention are for describing the embodiments and are not intended to limit the present invention. In this specification, the singular forms may In addition include the plural forms unless In detail stated in the phrase, and may include at least one of all combinations that may be combined in A, B, and C when described in "at least one (or more) of A (and), B. and C".

In addition, in describing the elements of the embodiments of the present invention, the terms such as first, second, A, B, (A, and (b) may be used. These terms are only used to distinguish the elements from other elements, and the terms are not limited to the essence, order, or order of the elements. Further, when an element is described as being "connected", "coupled", or "connected" to another element, it may include not only when the element is directly "connected" to, "coupled" to, or "connected" to other elements, but also when the element is "connected", "coupled", or "connected" by another element between the element and other elements.

Further, when described as being formed or disposed "on (over)" or "under (below)" of each element, the "on (over)" or "under (below)" may include not only when two elements are directly connected to each other, but also when one or more other elements are formed or disposed between two elements. Furthermore, when expressed as "on (over)" or "under (below)", it may include not only the upper direction but also the lower direction based on one element.

In addition, before describing the embodiments of the present invention, a first direction may refer to an x-axis direction shown in the drawings, and a second direction may be a different direction from the first direction. As an example, the second direction may refer to a y-axis direction shown in the drawing in a direction perpendicular to the first direction. In addition, a horizontal direction may refer to the first and second directions, and a vertical direction may refer to a direction perpendicular to at least one of the first and second directions. For example, the horizontal direction may refer to the x-axis and y-axis directions of the drawing, and the vertical direction may be a z-axis direction of the drawing and a direction perpendicular to the x-axis and v-axis directions.

FIG. 1 is a perspective view of a mask according to an embodiment, FIG. 2 is a front view of the mask according to the embodiment, and FIG. 3 is a rear view of the mask according to the embodiment.

Referring to FIGS. 1 to 3, a mask 2000 according to an embodiment may have a shape corresponding to a human face. The mask 2000 according to the embodiment may be provided in a predetermined size capable of covering a part or all of a user's face. The mask 2000 may include one surface facing the user's skin and the other surface opposite to the one surface and facing the outside, and the one surface of the mask 2000 may be made of a material that is harmless to the human body, so that it is harmless despite being in contact with the user's skin for a long time.

The mask 2000 may include a body 2001 having a shape corresponding to the user's face. The body 2001 may have a shape corresponding to the user's face and include an opening 2010 and a bending portion 2020.

The opening 2010 may be formed in a region corresponding to the user's eyes. The opening 2010 may be a region passing through one surface and the other surface of the mask 2000. At least one opening 2010 may be formed on the body 2001. As an example, the body 2001 may include one opening 2010. In this case, the opening 2010 may be formed in a region corresponding to both eyes and a part of the nose of the user. As another example, the body 2001 may include a plurality of openings 2010. In this case, the opening 2010 may be each formed in the left eye and the right eye of the user. Accordingly, w % ben the user wears the mask 2000, a view may be secured through the opening 2010.

The bending portion 2020 may be formed in a region corresponding to the user's nose. The bending portion 2020 may have a shape corresponding to the user's nose. As an example, the bending portion 2020 may have a shape bent from one surface of the mask 2000 toward the other surface, for example, a concave shape for mounting the user's nose. Accordingly, when the user wears the mask 2000, the mask 2000 may be mounted and fixed on the user's nose.

The mask 2000 may include an extension portion 2050 that extends from at least one end of the body 2001 toward the back of the user's head. The extension portion 2050 may be integrally formed with the body 2001. In addition, the extension portion 2050 may be formed separately from the body 2001 and may be coupled by a fastening member, but the embodiment is not limited thereto. In addition, the extension portion 2050 may include the same material as the body 2001, but the embodiment is not limited thereto.

As an example, the extension portion 2050 may include a first extension portion and a second extension portion that extend from both ends of the body 2001 toward the back of the user's head. The first and second extension portions may extend toward each of the user's left and right ears to overlap in a region behind the user's head.

In this case, a fixing member 2070 may be disposed on the extension portion 2050. In detail, the fixing member 2070 for fixing the extension portion 2050 may be disposed on the extension portion 2050. For example, the fixing member 2070 may be each disposed on one surface of the first extension portion facing the second extension portion and one surface of the second extension portion facing the first extension portion. As an example, the fixing member 2070 may include a Velcro, a hook, a button, a pin, or the like. However, the embodiment is not limited thereto, and the fixing member 2070 may include various fixing members capable of fixing the first and second extension portions. The first and second extension portions may be fixed to each other by the fixing member 2070. Accordingly, when the user wears the mask 2000, the mask 2000 may be disposed on and fixed on the set user's face and may be effectively adhered to the user's skin.

As another example, the first and second extensions may extend to a region adjacent to the user's ears. That is, the user may wear the mask 2000 like glasses. Therefore, the user may more easily wear and fix the mask and may easily take off the mask 2000 after use.

As still another example, the extension portion 2050 may extend from one end of the body 2001 toward the back of the users head. In detail, the extension portion 2050 may extend from one end of the body 2001 toward the back of the user's head and may be connected to the other end of the body 2001 after wrapping the back of the user's head. Accordingly, when the user wears the mask 2000, the mask 2000 may be disposed on and fixed on the set user's face and may be effectively adhered to the user's skin. In addition, the body 2001 may include a plurality of support members 2100 facing the users skin. A structure of the body 2001 will be described in detail with reference to FIGS. 12 to 15 described later.

The mask 2000 according to the embodiment may include a piezoelectric region 2030. The piezoelectric region 2030 may be a region corresponding to a region of the user's skin where wrinkles are likely to occur. For example, the piezoelectric region 2030 of the mask 2000 may include a first region 2031 defined as a region corresponding to the user's brow region, a second region 2033 defined as a region corresponding to the user's right eye rim, and a third region 2035 defined as a region corresponding to the user's left eye rim.

The piezoelectric part 1000 may be disposed on the body 2001. In detail, the piezoelectric part 1000 may be disposed on one surface of the mask 200X) facing the user's skin, for example, on one surface of the body 2001.

The piezoelectric part 1000 may be disposed in the region corresponding to the region of the user's skin where wrinkles are likely to occur. For example, the piezoelectric part 1000 may be disposed on the piezoelectric region 2030 of the mask 2000. The piezoelectric part 1000 may be disposed on at least one of the first region 2031, the second region 2033, and the third region 2035. As an example, the piezoelectric part 1000 may be disposed on the second region 2033 and the third region 2035 to provide ultrasonic energy to both eye rim regions of the user. As another example, the piezoelectric part 1000 may be formed on all of the first to third regions 2031, 2033, and 2035. Accordingly, it is possible to effectively provide ultrasonic energy to the user's eye rim regions and brow region.

That is, the mask 2000 according to the embodiment may be disposed on the user's skin, for example, on the region where wrinkles are likely to occur to provide ultrasonic energy to the skin. Accordingly, cracks may be formed in a stratum corneum of the user's skin to form a fine perforation, and drugs or cosmetics between the mask 2000 and the user's skin may be effectively provided to the user.

In addition, the piezoelectric part 1000 may be disposed on the support member 2100 of the body 2001. An arrangement relationship between the body 2001 and the piezoelectric part 1000 will be described in detail with reference to FIGS. 12 to 15 described later.

FIG. 4 is an exploded perspective view of a piezoelectric part according to an embodiment, and FIG. 5 is a top view of the piezoelectric part according to the embodiment. In addition, FIG. 6 is another top view of the piezoelectric part according to the embodiment, FIG. 7 is a cross-sectional view showing a cross-section A-A' of FIG. 6, and FIG. 8 is an enlarged view of region A1 of FIG. 7.

The piezoelectric part 1000 will be described in detail with reference to FIGS. 4 to 8. The piezoelectric part 1000 may include a first base layer 110, a first wiring 200, a piezoelectric element 400, a second wiring 300, and a second base layer 120. In detail, the piezoelectric part 1000 may include the first wiring 200, the piezoelectric element 400, the second wiring 300, and the second base layer 120 sequentially disposed on the first base layer 110.

The first base layer 110 may include a material harmless to the human body. In addition, the first base layer 110 may include a material having softness and elasticity. For example, the first base layer 110 may include at least one material of silicone, a thermoplastic resin, a thermoplastic silicone resin, a thermoplastic elastomer, a polyurethane elastomer, an ethylene vinyl acetate (EVA), a polyvinyl chloride (PVC) in which a harmless plasticizer and a stabilizer are added. Preferably, the first base layer 110 may include a silicone elastomer that is relatively light, may minimize irritation upon contact with the user's skin, and has a predetermined elasticity.

The first base layer 110 may reflect wavelengths emitted from the piezoelectric element 400 to be described later in a direction of one surface of the mask 2000. In detail, the first base layer 110 may reflect the wavelength of the piezoelectric element 400 toward one surface of the piezoelectric part 1000 facing the user's skin. That is, the first base layer 110 may be a reflective layer.

To this end, a thickness t1 of the first base layer 110 may be equal to or smaller than a thickness t2 of the second base layer 120 to be described later. In detail, the thickness t1 of the first base layer 110 may be equal to or smaller than the thickness t2 of the second base layer 120 in order to reflect the wavelengths emitted from the piezoelectric element 400 toward the first substrate 110 to the first base layer 110. That is, the second base layer 120 may be a base layer facing the user's skin, and the first base layer 110 may be a base layer disposed in a region opposite to the second base layer 120.

The thickness t1 of the first base layer 110 may be about 50 μm to about 10 mm. When the thickness t1 of the first base layer 510 is less than about 50 μm, the thickness t1 of the first base layer 510 is relatively small, so that components disposed on the first base layer 110 may not be effectively protected. In detail, when the piezoelectric part 1000 and the mask 2000 are elastically deformed and the first base layer 110 is elastically deformed, the wirings 200 and 300 and the piezoelectric element 400 on the first base layer 110 may not be effectively protected.

In addition, when the thickness t1 of the first base layer 110 exceeds about 10 mm, a thickness of the piezoelectric part 1000 and a thickness of the entire mask 2000 may be increased, and most of the wavelengths emitted from the piezoelectric element 400 toward the first substrate 110 pass through the first base layer 110, so that an amount of reflection in the direction of one surface of the mask 2000 may be small.

In addition, when the thickness t1 of the first base layer 110 exceeds about 10 mm, a required thickness of the second base layer 120 may be increased for reflection in the direction of one surface of the mask 2000, and a frequency domain ban of the wavelengths generated from the piezoelectric element 400 is high for reflection, and thus it may not be suitable for use in the mask 2000.

In addition, when the thickness t1 of the first base layer 110 exceeds about 10 mm, elastic deformation characteristics of the piezoelectric part 1000 and elastic deformation characteristics of the mask 2000 may be deteriorated. Accordingly, the piezoelectric part 1000 and the mask 2000 may not be elastically deformed effectively in a form corresponding to the user's skin, and thus adhesion to the skin may be deteriorated.

Therefore, it is preferable that the thickness t1 of the first base layer 110 satisfies the above-described range in order to prevent the above-described problems. More preferably, the thickness t1 of the first base layer 110 may be about 100 μm to about 1000 μm. That is, it is preferable that the first base layer 110 has a thickness range of about 100 μm to about 1000 μm in consideration of reliability, reflective properties, variability, thickness, weight, and ultrasonic impedance characteristics of the piezoelectric part 1000.

In addition, although not shown in the drawing, the first base layer 110 may have grooves, pores, or the like formed therein in order to effectively reflect the wavelengths generated from the piezoelectric element 400. For example, the grooves and pores may be disposed in a region overlapping the piezoelectric element 400 for effective reflection, but the embodiment is not limited thereto.

The first wiring 200 may be disposed on the first base layer 110. The first wiring 200 may be disposed on one surface of the first base layer 110 facing the piezoelectric element 400. The first wiring 200 may extend in a first direction (x-axis direction) on the first base layer 110. The first wiring 200 may be in direct contact with one surface of the first base layer 110. The first wiring 200 may be formed on one surface of the first base layer 110 by a process such as deposition, printing, bonding, or the like. The first wiring 200 may be electrically connected to the piezoelectric element 400.

The first wiring 200 may include a conductive material. As an example, the first wiring 200 may include at least one metal of aluminum (Al), copper (Cu), silver (Ag), gold (Au), chromium (Cr), nickel (Ni), molybdenum (Mo), titanium (Ti), and alloys thereof. In addition, the first wiring 200 may include a non-metal such as carbon, and the like, and may include a conductive elastic body.

The first wiring 200 may have a single layer or a multiple layer structure. As an example, the first wiring 200 may have a single layer structure including one selected from the above-described materials. In addition, the first wiring 200 may have a multiple layer structure including a metal material selected from the above-described materials and the conductive elastic body.

The first wiring 200 may include a plurality of first sub-wirings 201 disposed on the first base layer 110. Each of the plurality of first sub-wirings 201 may extend in a first direction and may be disposed to be spaced apart from each other in a second direction different from the first direction. The plurality of first sub-wirings 201 may be electrically connected to each other. Here, the second direction may be a direction different from the first direction and a direction perpendicular to the first direction, but the embodiment is not limited thereto.

A thickness of the first sub-wiring 201 may be about 2 μm to about 50 μm. In detail, the thickness of the first sub-wiring 201 may be about 2 μm to about 40 μm. When the thickness of the first sub-wiring 201 is less than about 2 μm, electrical characteristics may be deteriorated, and it may be difficult to form uniformly. In addition, when the thickness of the first sub-wiring 201 exceeds about 50 μm, the overall thickness of the piezoelectric part 1000 and the overall thickness of the mask 2000 may be increased, and a manufacturing time of the first wiring 210 may be increased. In addition, the thickness of the first sub-wiring 201 is too thick, and thus stretchable characteristics may be deteriorated. Preferably, the thickness of the first sub-wiring 201 may be about 5 μm to about 35 μm or less in consideration of stretchable characteristics in the horizontal direction, reliability, and process efficiency.

In addition, a line width of the first sub-wiring 201 may be about 50 μm to about 500 μm. In detail, the line width of the first sub-wiring 201 may be about 100 μm to about 450 μm. The line width of the first sub-wiring 201 may be greater than the thickness of the first sub-wiring 201. When the line width of the first sub-wiring 201 is less than about 50 μm, the reliability may be deteriorated, and when the line width of the first sub-wiring 201 exceeds about 500 μm, an elongation may be decreased and the stretchable characteristics may be deteriorated. Preferably, the line width of the first sub-wiring 201 may be about 100 μm to about 400 μm in consideration of the stretchable characteristics.

The first wiring 200 may include a first connection portion 210 and a first extension portion 220. For example, one of the first sub-wirings 201 may include the first connection portion 210 and the first extension portion 220 connected to the first connection portion 210.

The first connection portion 210 may be disposed in a region corresponding to a lower surface of the piezoelectric element 400. In detail, the first connection portion 210 may be disposed in a region overlapping the lower surface of the piezoelectric element 400 in the vertical direction. The first connection portion 210 may face the lower surface of the piezoelectric element 400. The first connection portion 210 may be provided in a number corresponding to the piezoelectric element 400.

The first connection portion 210 may have a shape corresponding to the lower surface of the piezoelectric element 400. The first connection portion 210 may have a width corresponding to the lower surface of the piezoelectric element 400. As an example, a width of the first connection portion 210 in the horizontal direction may be equal to or smaller than a width of the lower surface of the piezoelectric element 400 in the horizontal direction. In detail, the width of the first connection portion 210 in the horizontal direction may be about 50% to about 100% of the width of the lower surface of the piezoelectric element 400 in the horizontal direction. When the width of the first connection portion 210 in the horizontal direction is less than about 50%, electrical characteristics between the first wiring 200 and the piezoelectric element 400 may be deteriorated. In addition, when the width of the first connection portion 210 in the horizontal direction is greater than the width of the lower surface of the piezoelectric element 400, the transmittance of ultrasonic energy may be deteriorated. Therefore, it is preferable that the width of the first connection portion 210 in the horizontal direction satisfies the above-described range.

The first extension portion 220 may extend in the first direction from the first connection portion 210. The first extension portion 220 may be disposed between a plurality of first connection portions 210. In detail, the first extension portion 220 may be disposed between the first connection portions 210 spaced apart in the first direction. That is, the first extension portion 220 may connect between adjacent first connection portions 210.

The first wiring 200 may have various shapes. For example, when viewed in a plane, each of the plurality of first sub-wirings 201 may extend in the first direction in a linear shape as shown in FIG. 5. In detail, the plurality of first sub-wirings 201 may be spaced apart from the adjacent first sub-wirings 201 in the second direction at equivalent intervals and may extend in the first direction in the linear shape. That is, the first extension portion 220 of the first wiring 200 may have the linear shape extending in the first direction.

Alternatively, when viewed in a plane, each of the plurality of first sub-wirings 201 may extend in the first direction in a curved shape as shown in FIG. 6. For example, each of the plurality of first sub-wirings 201 may be provided in a form in which a wavy pattern is repeated. That is, the first extension portion 220 of the first wiring 200 may have the curved shape extending in the first direction.

In this case, the first extension portion 220 may have a curvature pattern of about 3R to about 20R (mm). Accordingly, when the piezoelectric part 1000 and the mask 2000 are stretched or contracted in one direction, the first wiring 200 may have the stretchable characteristics and may not be cut. Preferably, the first extension portion 220 may have a curvature pattern of about 5R to about 15R (mm). In addition, the first extension portion 220 may have an elongation of about 10% to about 50%. Accordingly, the first wiring 200 may have more improved stretchable characteristics, thereby improving reliability and improving adhesion to the user's skin.

Still alternatively, although not shown in the drawing, the first extension portion 220 may have a shape in which a pattern in which a straight line and a curve extending in the first direction are mixed is repeated. For example, when viewed from a plane, the first extension portion 220 positioned in a region overlapping a relatively curved region (cheekbones, cheeks, a region between eyes and temples, etc.) of the user's face may be provided in the curved shape, and the first extension portion 220 positioned in a region overlapping a relatively planar region (brow, etc.) may be provided in the linear shape. Accordingly, when the user wears the mask 2000, it is possible to prevent the first wiring 200 from being damaged due to deformation of the piezoelectric part 1000. In addition, the first extension portion 220 may be provided in a form in which the straight line and the curve are mixed to maintain electrical characteristics and reduce a ratio occupied by the first wiring 200. Therefore, the embodiment may reduce manufacturing costs of the first wiring 200 and minimize the loss of ultrasonic energy emitted from the piezoelectric element 400.

The piezoelectric element 400 may be disposed on the first base layer 110. The piezoelectric element 400 may be disposed on the first wiring 200. In detail, the piezoelectric element 400 may be disposed on the first extension portion 220 of the first wiring 200 to be electrically connected to the first wiring 200.

The piezoelectric element 400 may include a ceramic material. As an example, the piezoelectric element 400 may include at least one of ZnO, AlN, LiNbO$_4$, lead antimony stannate, lead magnesium tantalate, lead nickel tantalate, titanates, tungstates, zirconates, or lead including lead zirconate titanate [Pb(Zr$_x$Ti$_{1-x}$)O$_3$(PZT)], lead lanthanum zirconate titanate (PLZT), lead niobium Zirconate titanate (PNZT), BaTiO$_3$, SrTO$_3$, lead magnesium niobate, lead nickel niobate, lead manganese niobate, lead zinc niobate, lead including lead titanate, barium, bismuth, or niobates of strontium.

The piezoelectric element 400 may be disposed on the first wiring 200 in plural. The plurality of piezoelectric elements 400 may be disposed to be spaced apart from each other on the first sub-wiring 201. For example, the plurality of piezoelectric elements 400 may be disposed on the first connection portion 210 on the first sub-wiring 201. In detail, one piezoelectric element 400 may be disposed on one first connection portion 210. A center of the lower surface of the piezoelectric element 400 may overlap the first sub-wiring 201 in the vertical direction. In detail, the center of the lower surface of the piezoelectric element 400 may overlap the first connection portion 210. In more detail, the center of the lower surface of the piezoelectric element 400 may overlap a center of the first connection portion 210.

The plurality of piezoelectric elements 400 may be spaced apart at equivalent intervals on the first sub-wiring 201. For example, the plurality of piezoelectric elements 400 disposed on one first sub-wiring 201 may be disposed at equivalent intervals based on the first direction. In addition, the piezoelectric elements 400 disposed on the adjacent first sub-wirings 201 may be disposed at equivalent intervals based on the second direction. Accordingly, a virtual line connecting centers of the adjacent plurality of piezoelectric elements 400 in the first direction and the second direction may have a mesh shape.

In addition, a piezoelectric element 400 disposed on one first sub-wiring 201 may overlap or not overlap a piezoelectric element 400 disposed on the first sub-wiring 201 closest to the one first sub-wiring 201 in the second direction. As an example, when viewed in a plane, the piezoelectric element 400 may be disposed in a zigzag shape on the adjacent first sub-wiring 201

In addition, a distance between some of the piezoelectric elements 400 may be disposed at equivalent intervals, and the remaining piezoelectric elements 400 may not be disposed at equivalent intervals. For example, the distance between the piezoelectric elements 400 may be disposed at equivalent intervals in a region overlapping a relatively planar region of a surface of the user's face. However, the distance between the piezoelectric elements 400 may not be disposed at equivalent intervals in a region overlapping a relatively curved skin region. That is, the distance between the piezoelectric elements 400 may be relatively narrow or large depending on the degree of curvature of the skin surface. As an example, the distance between the piezoelectric elements 400 of the region overlapping the curved region such as the cheekbones, the cheeks, the region between eyes and temples, etc. of the user, may be relatively narrow. Accordingly, the piezoelectric part 1000 according to the embodiment may effectively provide ultrasonic energy even to the curved skin.

The piezoelectric element 400 may be disposed on the entire region of the piezoelectric part 1000 to generate evenly the ultrasonic energy. For example, the piezoelectric element 400 may generate ultrasonic energy of about 1 MHz or less by an applied current. In detail, the piezoelectric element 400 may generate ultrasonic energy of about 10 KHz to about 1 MHz. In more detail, the piezoelectric element 400 may generate ultrasonic energy of about 50 KHz to about 800 KHz. The ultrasonic energy generated by the piezoelectric element 400 may move in a direction of one surface of the piezoelectric part 1000, for example, in a direction of one surface of the mask 2000 and may be transmitted to the user's skin to massage the user's skin.

A thickness of the piezoelectric element 400 may be about 1500 μm or less. In detail, the thickness of the piezoelectric element 400 may be about 1200 μm or less. Preferably, the thickness of the piezoelectric element 400 may be about 1000 μm or less. It is preferable that the thickness of the piezoelectric element 400 satisfies the above-described range in consideration of the overall thickness and variable characteristics of the piezoelectric part 1000.

The piezoelectric element 400 may have various shapes. For example, the piezoelectric element 400 may have a polygonal column shape in which lower and upper surfaces are polygonal, and the lower and upper surfaces may have a circular column shape. In addition, the piezoelectric element 400 may have a pillar shape in which one surface of the lower and upper surfaces is a polygonal and the other surface is circular. As an example, a region of at least one area of the lower surface and the upper surface of the piezoelectric element 400 may be about 100 mm² or less.

As described above, the piezoelectric element 400 may have various pillar shapes, and intensity and an oscillation direction of ultrasonic energy generated according to the pillar shape may be controlled. In addition, the intensity of ultrasonic energy transmitted to the user's skin may be adjusted according to a size, arrangement interval, arrangement density, and the like of the piezoelectric element 400.

The piezoelectric element 400 may generate various waves. As an example, the piezoelectric element 400 may generate at least one wave of a transverse wave in which a traveling direction of wave and a vibration direction of medium are perpendicular, and a longitudinal wave in which the traveling direction of wave and the vibration direction of medium are the same. In addition, the piezoelectric element 400 may multiple-resonate. For example, the piezoelectric element 400 may include at least one via hole and may multiple-resonate by the formed via holes. In this case, an upper area of the via holes may be about 10% to about 45% of an area of an upper surface of the piezoelectric element 400 for multiple resonance. In addition, when the piezoelectric element 400 multiple-resonates by the via holes, the number of multiple resonant frequency regions may correspond to the number of the via holes. That is, the piezoelectric element 400 may emit wavelengths of various frequency ranges, for example, ultrasonic energy, as the number of the via holes increases in a set number range of via holes.

The second base layer 120 may be disposed on the piezoelectric element 400. The second base layer 120 is a portion that may be in contact with the skin while facing the user's skin, and may include a material harmless to the human body. In addition, the second base layer 120 may include a material having softness and elasticity. For example, the second base layer 120 may include at least one material of silicone, a thermoplastic resin, a thermoplastic silicone resin, a thermoplastic elastomer, a polyurethane elastomer, an ethylene vinyl acetate (EVA), a polyvinyl chloride (PVC) in which a harmless plasticizer and a stabilizer are added. Preferably, the second base layer 120 may include a silicone elastomer that is relatively light, may minimize irritation upon contact with the user's skin, and has a predetermined elasticity. The first base layer 110 may be provided with the same material as the second base layer 120.

The second base layer 120 may pass through the wavelengths emitted from the piezoelectric element 400 in the direction of one surface of the piezoelectric part 1000 to transmit the wavelengths to the user's skin. That is, the second base layer 120 is transmission layer and may be a matching layer.

To this end, the thickness t2 of the second base layer 120 may vary depending on an impedance of the second base layer 120 and a driving frequency of the piezoelectric element 300. In addition, the thickness t2 of the second base layer 120 may be equal to or greater than the thickness of the first base layer 110.

As an example, when the driving frequency of the piezoelectric element 400 is about 1 MHz or less, the thickness t2 of the second base layer 120 may be about 50 µm to about 1 mm. When the thickness t2 of the second base layer 120 is less than about 50 µm, the thickness t2 of the second base layer 120 is relatively small, so that components disposed on the second base layer 120 may not be effectively protected. In detail, when the mask 2000 is elastically deformed and the second base layer 120 is elastically deformed, the wirings 200 and 300 and the piezoelectric element 400 on the second base layer 120 may not be effectively protected.

In addition, when the thickness t2 of the second base layer 120 exceeds about 10 mm, the overall thickness of the piezoelectric part 1000 and the overall thickness of the mask 2000 may be increased. Accordingly, the elastic deformation characteristics of the piezoelectric part 1000 may be deteriorated, and the mask 1000 may not be elastically deformed effectively in a form corresponding to the user's skin, and thus adhesion to the skin may be deteriorated.

Therefore, it is preferable that the thickness t2 of the second base layer 120 satisfies the above-described range in order to effectively pass through the wavelengths emitted from the piezoelectric element 400. Preferably, the thickness t2 of the second base layer 120 may have a thickness range of 100 µm to about 1000 µm in consideration of reliability, transmission characteristics, variability, thickness, weight, and ultrasonic impedance characteristics of the mask 2000 to be manufactured.

That is, some of the ultrasonic energy emitted from the piezoelectric element 400 according to the embodiment may be emitted toward the second base layer 120 and pass through the second base layer 120 to be transmitted to the user's skin. In addition, another part of the ultrasonic energy may be emitted toward the first base layer 110 and reflected toward the second base layer 120 by the first base layer 110. Thereafter, the reflected ultrasonic energy may pass through the second base layer 120 to be transferred to the user's skin.

The second wiring 300 may be disposed on the second base layer 120. The second wiring 300 may be disposed on one surface of the second base layer 120 facing the piezoelectric element 400. The second wiring 300 may extend in a different direction from the first wiring 200 on the second base layer 120. For example, the second wiring 300 may extend in a second direction (y-axis direction) perpendicular to the first direction. The second wiring 300 may be in direct contact with one surface of the second base layer 120. The second wiring 300 may be formed on one surface of the second base layer 120 by a process such as deposition, printing, bonding, or the like. The second wiring 300 may be electrically connected to the piezoelectric element 400.

The second wiring 300 may include a conductive material. As an example, the second wiring 300 may include at least one metal of aluminum (Al), copper (Cu), silver (Ag), gold (Au), chromium (Cr), nickel (Ni), molybdenum (Mo), titanium (Ti), and alloys thereof. In addition, the second wiring 300 may include a non-metal such as carbon, and the like, and may include a conductive elastic body. The second wiring 300 may include the same material as the first wiring 200.

The second wiring 300 may have a single layer or a multiple layer structure. As an example, the second wiring

300 may have a single layer structure including one selected from the above-described materials. In addition, the second wiring 300 may have a multiple layer structure including a metal selected from the above-described materials and the conductive elastic body. The second wiring 300 may include the same material as the first wiring 200.

The second wiring 300 may include a plurality of second sub-wirings 301 disposed on the second base layer 120. Each of the plurality of second sub-wirings 301 may extend in the second direction and may be disposed to be spaced apart from each other in the first direction. The plurality of second sub-wirings 301 may be electrically connected to each other.

A thickness of the second sub-wiring 301 may be about 2 µm to about 50 µm. In detail, the thickness of the second sub-wiring 301 may be about 2 µm to about 40 µm. When the thickness of the second sub-wiring 301 is less than about 2 µm, electrical characteristics may be deteriorated, and it may be difficult to form uniformly. In addition, when the thickness of the second sub-wiring 301 exceeds about 50 µm, the overall thickness of the piezoelectric part 1000 and the overall thickness of the mask 2000 may be increased, and a manufacturing time of the second wire 300 may be increased. In addition, the thickness of the second sub-wiring 301 is too thick, and thus stretchable characteristics may be deteriorated. Preferably, the thickness of the second sub-wiring 301 may be about 5 µm to about 35 µm or less in consideration of stretchable characteristics in the horizontal direction, reliability, and process efficiency.

In addition, a line width of the second sub-wiring 301 may be about 50 µm to about 500 µm. In detail, the line width of the second sub-wiring 301 may be about 100 µm to about 450 µm. The line width of the second sub-wiring 301 may be greater than the thickness of the second sub-wiring 301. When the line width of the second sub-wiring 301 is less than about 50 µm, the reliability may be degraded, and when the line width of the second sub-wiring 301 exceeds about 500 µm, an elongation may be decreased and the stretchable characteristics may be deteriorated. Preferably, the line width of the second sub-wiring 301 may be about 100 µm to about 400 µm in consideration of the stretchable characteristics.

The second wiring 300 may include a second connection portion 310 and a second extension portion 320. For example, one of the second sub-wirings 301 may include the second connection portion 310 and the second extension portion 320 connected to the second connection portion 310.

The second connection portion 310 may be disposed in a region corresponding to an upper surface of the piezoelectric element 400. In detail, the second connection portion 310 may be disposed in a region overlapping the upper surface of the piezoelectric element 400 in the vertical direction. The second connection portion 310 may face the upper surface of the piezoelectric element 400. The second connection portion 310 may be provided in a number corresponding to the piezoelectric element 400.

The second connection portion 310 may have a shape corresponding to the upper surface of the piezoelectric element 400. The second connection portion 310 may have a width corresponding to the upper surface of the piezoelectric element 400. As an example, a width of the second connection portion 310 in the horizontal direction may be equal to or smaller than a width of the upper surface of the piezoelectric element 400 in the horizontal direction. In detail, the width of the second connection portion 310 in the horizontal direction may be about 50% to about 100% of the width of the upper surface of the piezoelectric element 400 in the horizontal direction. When the width of the second connection portion 310 in the horizontal direction is less than about 50%, electrical characteristics between the second wiring 300 and the piezoelectric element 400 may be deteriorated. In addition, when the width of the second connection portion 310 in the horizontal direction is greater than the width of the lower surface of the piezoelectric element 400, the transmittance of ultrasonic energy may be deteriorated. Therefore, it is preferable that the width of the second connection portion 310 in the horizontal direction satisfies the above-described range.

The second extension portion 320 may extend in the second direction from the second connection portion 310. The second extension portion 320 may be disposed between a plurality of second connection portions 310. In detail, the second extension portion 320 may be disposed between the second connection portions 310 spaced apart in the second direction. That is, the second extension portion 320 may connect between adjacent second connection portions 310.

The second wiring 300 may have various shapes. For example, when viewed in a plane, each of the plurality of second sub-wirings 301 may extend in the second direction in the linear shape as shown in FIG. 5. In detail, the plurality of second sub-wirings 301 may be spaced apart from the adjacent second sub-wirings 301 in the first direction at equivalent intervals and may extend in the second direction in the linear shape. That is, the second extension portion 320 of the second wiring 300 may have the linear shape extending in the second direction.

Alternatively, when viewed in a plane, each of the plurality of second sub-wirings 301 may extend in the second direction in the curved shape as shown in FIG. 6. For example, each of the plurality of second sub-wirings 301 may be provided in a form in which a wavy pattern is repeated. That is, the second extension portion 320 of the second wiring 300 may have the curved shape extending in the second direction.

In this case, the second extension portion 320 may have a curvature pattern of about 3R to about 20R (mm). Accordingly, when the piezoelectric part 1000 and the mask 2000 are stretched or contracted in one direction, the second wiring 300 may have the stretchable characteristics and may not be cut. Preferably, the second extension portion 320 may have a curvature pattern of about 5R to about 15R (mm). In addition, the second extension portion 320 may have an elongation of about 10% to about 50%. Accordingly, the second wiring 300 may have more improved stretchable characteristics, thereby improving reliability and improving adhesion to the user's skin.

Still alternatively, although not shown in the drawing, the second extension portion 320 may have a shape in which a pattern in which a straight line and a curve extending in the first direction are mixed is repeated. For example, when viewed from a plane, the second extension portion 320 positioned in a region overlapping a relatively curved region (cheekbones, cheeks, a region between eyes and temples, etc.) of the user's face may be provided in the curved shape, and the second extension portion 320 positioned in a region overlapping a relatively planar region (brow, etc.) may be provided in the linear shape. Accordingly, when the user wears the mask 2000, it is possible to prevent the second wiring 300 from being damaged due to deformation of the piezoelectric part 1000. In addition, the second extension portion 320 may be provided in a form in which the straight line and the curve are mixed to maintain electrical characteristics and reduce a ratio occupied by the second wiring 300. Therefore, the embodiment may reduce manufacturing costs of the second wiring 300 and minimize the loss of ultrasonic energy emitted from the piezoelectric element 400.

The first wiring 200 and the second wiring 300 may be disposed to cross each other. In detail, when viewed in a plane as shown in FIGS. 5 and 6, the first sub-wiring 201 and the second sub-wiring 301 may be disposed to cross each other in a mesh shape, and, an open region in which the wirings 200 and 300 are not disposed may be formed between the sub-wirings 201 and 301.

The piezoelectric element 400 may be disposed on a region where the first wiring 200 and the second wiring 300 cross each other. In detail, a center of the piezoelectric element 400 may overlap an intersection point of the first sub-wiring 201 and the second sub-wiring 301. In more detail, a center of each of the lower and upper surfaces of the piezoelectric element 400 may overlap a center of the first connection portion 210 of the first wiring 200 and a center of the second connection portion 310 of the second wiring 300.

In addition, although not shown in the drawings, a vibration member (not shown) may be further disposed on the piezoelectric element. In order to improve vibration characteristics of the piezoelectric element 400, the vibration member may be further disposed on the upper surface of the piezoelectric element 400. For example, the vibration member may be a vibration plate. The vibration member may be disposed between the piezoelectric element 400 and the second wiring 300.

The vibration member may be electrically connected to the piezoelectric element 400. The vibration member may include a metal material. As an example, the vibration member may include at least one metal of aluminum (Al), copper (Cu), zinc (Zn), iron (Fe), nickel (Ni), chromium (Cr), silver (Ag), gold (Pt), stainless steel (SUS), and alloys thereof.

The vibration member may have a shape corresponding to the piezoelectric element 400. For example, the vibration member may have a planar shape corresponding to the upper surface of the piezoelectric element 400. In addition, the vibration member may have a width in the horizontal direction corresponding to the upper surface of the piezoelectric element 400.

A thickness of the vibration member may be about 1500 μm or less. In detail, the thickness of the vibration member may be about 1200 μm or less. Preferably, the thickness of the vibration member may be about 1000 μm or less. It is preferable that the thickness of the vibration member satisfies the above-described range in consideration of the deformation characteristics of the piezoelectric part 1000 and the vibration characteristics of the piezoelectric element 400.

The piezoelectric part 1000 according to the embodiment may include the protective layer 550. The protective layer 550 may be disposed between the first base layer 110 and the second base layer 120. The protective layer 550 may be disposed in direct contact with one surface of the first base layer 110 and one surface of the second base layer 120.

The protective layer 550 may be disposed between the first base layer 110 and the second base layer 120 to protect the piezoelectric element 400. In detail, the protective layer 550 may be disposed to surround the piezoelectric element 400 and the wirings 200 and 300 between the base layers 110 and 120 to protect the components.

The protective layer 550 may include a material having softness and elasticity. For example, the protective layer 550 may include at least one material of silicone, a thermoplastic resin, a thermoplastic silicone resin, a thermoplastic elastomer, a polyurethane elastomer, an ethylene vinyl acetate (EVA), a polyvinyl chloride (PVC) in which a harmless plasticizer and a stabilizer are added. The protective layer 550 may be preferable to include a silicone elastomer that is relatively light, may minimize irritation upon contact with the user's skin, and has a predetermined elasticity.

The protective layer 550 may be connected to the first base layer 110 and the second base layer 120. For example, the protective layer 550 may be integrally formed with the first base layer 110 and the second base layer 120. The protective layer 550 may be physically connected to the first base layer 110 and the second base layer 120 to protect components disposed therein.

The protective layer 550 may include the same material as the first base layer 110 and the second base layer 120. That is, the first base layer 110, the second base layer 120, and the protective layer 550 may include the same kind of material, thereby having an improved bonding force.

A connection relationship between the piezoelectric element 400, the first wiring 200, and the second wiring 300 will be described in more detail with reference to FIG. 8.

Referring to FIG. 8, the piezoelectric element 400 may be electrically connected to the first wiring 200 and the second wiring 300. In detail, the piezoelectric element 400 may include a first electrode 410 disposed on a lower surface thereof. The first electrode 410 may be disposed in a region of about 80% or more of the entire region of the lower surface of the piezoelectric element 400 in consideration of electrical characteristics. The first electrode 410 may be disposed in a region of about 90% of the entire region of the lower surface of the piezoelectric element 400. In addition, the first electrode 410 may be disposed on the entire region of the lower surface of the piezoelectric element 400.

The first electrode 410 may include a conductive material. As an example, the first electrode 410 may include a metal material. In detail, the first electrode 410 may include at least one metal of aluminum (Al), copper (Cu), silver (Ag), gold (Au), chromium (Cr), nickel (Ni), molybdenum (Mo), titanium (Ti), and alloys thereof.

The first electrode 410 may be disposed facing the first wire 200 and may be electrically connected to the first wire 200. In detail, a first bonding layer 451 may be disposed between the first electrode 410 and the first wiring 200. The first bonding layer 451 may physically and electrically connect the first electrode 410 and the first wiring 200. An overlapping ratio between the first bonding layer 451 and the first wiring 200 may be about 20% or more in consideration of physical and electrical characteristics. In detail, an overlapping ratio of one surface of the first wiring 200 facing the piezoelectric element 400 and the first bonding layer 451 may be about 20% or more.

The first bonding layer 451 may include at least one metal of aluminum (Al), copper (Cu), silver (Ag), gold (Au), chromium (Cr), nickel (Ni), molybdenum (Mo), titanium (Ti), and alloys thereof.

A thickness of the first bonding layer 451 may be about 100 µm or less. In detail, the thickness of the first bonding layer 451 may be about 20 µm to about 80 µM. Preferably, the thickness of the first bonding layer 451 may be about 30 µm to about 60 µm.

The first bonding layer 451 may be disposed between the first electrode 410 and the first wiring 200 to serve as a conductive adhesive. As an example, the first bonding layer 451 may be applied in a form of a paste on the first wiring 200, and the piezoelectric element 400 including the first electrode 410 may be disposed on the first bonding layer 451. Accordingly, the piezoelectric element 400 may be physically and electrically connected to the first wiring 200.

The piezoelectric element 400 may include a second electrode 420 disposed on an upper surface thereof. The second electrode 420 may be disposed in a region of about 80% or more of the entire region of the upper surface of the piezoelectric element 400 in consideration of electrical characteristics. In detail, the second electrode 420 may be disposed in a region of about 90% of the entire region of the upper surface of the piezoelectric element 400. In addition, the second electrode 420 may be disposed on the entire region of the lower surface of the piezoelectric element 400.

The second electrode 420 may include a conductive material. As an example, the second electrode 420 may include a metal material. In detail, the second electrode 420 may include at least one metal of aluminum (Al), copper (Cu), silver (Ag), gold (Au), chromium (Cr), nickel (Ni), molybdenum (Mo), titanium (Ti), and alloys thereof.

The second electrode 420 may be disposed facing the second wiring 300 and may be electrically connected to the second wiring 300. In detail, a second bonding layer 452 may be disposed between the second electrode 420 and the second wiring 300. The second bonding layer 452 may physically and electrically connect the second electrode 420 and the second wiring 300. An overlapping ratio between the second bonding layer 452 and the second wiring 300 may be about 20% or more in consideration of physical and electrical characteristics. In detail, an overlapping ratio between one surface of the second wiring 300 facing the piezoelectric element 400 and the second bonding layer 452 may be about 20% or more.

The second bonding layer 452 may include at least one metal of aluminum (Al), copper (Cu), silver (Ag), gold (Au), chromium (Cr), nickel (Ni), molybdenum (Mo), titanium (Ti), and alloys thereof.

A thickness of the second bonding layer 452 may be about 100 µm or less. In detail, the thickness of the second bonding layer 452 may be about 20 µm to about 80 µm. Preferably, the thickness of the second bonding layer 452 may be about 30 µm to about 60 µm.

The second bonding layer 452 may be disposed between the second electrode 420 and the second wiring 300 to serve as a conductive adhesive. As an example, the second bonding layer 452 may be applied in the form of the paste on the second wiring 300, and the piezoelectric element 400 including the second electrode 420 may be disposed on the second bonding layer 452. Accordingly, the piezoelectric element 400 may be physically and electrically connected to the second wiring 300.

The thickness of the first bonding layer 451 may be the same as or different from the thickness of the second bonding layer 452. As an example, the thickness of the first bonding layer 451 may be provided with the same thickness as the second bonding layer 452 to improve the variability of the mask 2000. As another example, the thickness of the first bonding layer 451 may be greater than the thickness of the second bonding layer 452. Accordingly, the wavelengths emitted from the piezoelectric element 400 toward the first base layer 110 may be reflected by the first bonding layer 451 to move toward the second base layer 120.

The protective layer 550 may be disposed to surround the piezoelectric element 400, the first wiring 200, the second wiring 300, the first electrode 410, the second electrode 420, the first bonding layer 451, and the second bonding layer 452, and it is possible to prevent the components from being exposed to the outside.

FIG. 9 is another exploded perspective view of a piezoelectric part according to an embodiment, and FIG. 10 is a cross-sectional view of the piezoelectric part of FIG. 9. In the description using FIGS. 9 and 10, descriptions of configurations the same as or similar to those of the above-described piezoelectric part are omitted, and the same reference numerals are assigned to the same as or similar to the configurations.

Referring to FIGS. 9 and 10, a piezoelectric part 1000 according to an embodiment may further include a first substrate 510 and a second substrate 520.

The first substrate 510 may be disposed on the first base layer 110. The first substrate 510 may be disposed between the first base layer 110 and the first wiring 200. The first substrate 510 may be in direct contact with one surface of the first base layer 110. In this case, the first wiring 200 may be spaced apart from the first base layer 110 and may be in direct contact with the first substrate 510.

The first substrate 510 may be transparent and include a material in consideration of moisture barrier properties, thermal stability, and the like. In addition, the first substrate 510 may include a material that has flexibility and is elastically deformed depending on a shape of the user's skin. As an example, the first substrate 510 may include a resin material such as polyethylene terephthalate (PET), polyethylene naphthalate (PEN), polyimide (PI), and the like. The first substrate 510 may be provided in a form of a film.

The first substrate 510 may have a thickness of about 0.5 μm to about 5 μm or less. When the thickness of the first substrate 510 is less than about 0.5 μm, there may be a problem that a region of the first substrate 510 that overlaps the components is sagged by a weight of components disposed on the first substrate 510, for example, the piezoelectric element 400 or the like. Accordingly, reliability of the first substrate 510 may be deteriorated, and a problem of alignment of the components disposed on the first substrate 510 may occur. In addition, when the thickness of the first substrate 510 exceeds about 5 μm, the overall thickness of the piezoelectric part 1000 and the overall thickness of the mask 2000 may be increased. Accordingly, there is a problem that the piezoelectric part 1000 may not be elastically deformed efficiently depending on the shape of the user's skin, so that the piezoelectric part 1000 may not be effectively adhered to the user's skin. Preferably, the first substrate 510 may have a thickness of about 0.5 μm to about 3 μm. When the thickness of the first substrate 510 satisfies the above-described range, the piezoelectric part 1000 may be elastically deformed efficiently in a form corresponding to the user's skin, and the overall thickness and weight of the mask 2000 may be decreased while maintaining reliability and alignment characteristics.

The second substrate 520 may be disposed on the second base layer 120. The second substrate 520 may be disposed between the second base layer 120 and the second wiring 300. The second substrate 520 may be in direct contact with one surface of the second base layer 120. In this case, the second wiring 300 may be spaced apart from the second base layer 120 and may be in direct contact with the second substrate 520.

The second substrate 520 may be transparent and include a material in consideration of moisture barrier properties, thermal stability, and the like. In addition, the second substrate 520 may include a material that has flexibility and is elastically deformed depending on the shape of the user's skin. As an example, the second substrate 520 may include the resin material such as polyethylene terephthalate (PET), polyethylene naphthalate (PEN), polyimide (PI), and the like. The second substrate 520 may be provided in a form of a film. The second substrate 520 may have the same material and shape as the first substrate 510, but the embodiment is not limited thereto.

The second substrate 520 may have a thickness of about 0.5 μm to about 5 μm or less. When the thickness of the second substrate 520 is less than about 0.5 μm, there may be a problem that a region of the second substrate 520 that overlaps the components is sagged by a weight of components disposed on the second substrate 520, for example, the piezoelectric element 400 or the like. Accordingly, reliability of the second substrate 520 may be deteriorated, and a problem of alignment of the components disposed on the second substrate 520 may occur. In addition, when the thickness of the second substrate 520 exceeds about 5 μm, the overall thickness of the piezoelectric part 1000 and the overall thickness of the mask 2000 may be increased. Accordingly, there is a problem that the piezoelectric part 1000 may not be elastically deformed efficiently depending on the shape of the user's skin, so that the piezoelectric part 1000 may not be effectively adhered to the user's skin. Preferably, the second substrate 520 may have a thickness of about 0.5 μm to about 3 μm. When the thickness of the second substrate 520 satisfies the above-described range, the piezoelectric part 1000 may be elastically deformed efficiently in a form corresponding to the user's skin, and the overall thickness and weight of the mask 2000 may be decreased while maintaining reliability and alignment characteristics. The second substrate 520 may have the same thickness as the first substrate 510, but the embodiment is not limited thereto.

In the embodiment, as the first substrate 510 and the second substrate 520 are added, the alignment characteristics of the piezoelectric element 400 may be improved. In addition, as the first substrate 510 and the second substrate 520 are added, an inflow path of moisture and foreign substances introduced from the outside of the piezoelectric part 1000 to the inside may be increased, so that the piezoelectric part 1000 may have improved reliability.

FIG. 11 is a cross-sectional view showing an example in which a protrusion is provided on a piezoelectric part according to an embodiment. In the description using FIG. 11, descriptions of configurations the same as or similar to those of the above-described piezoelectric part are omitted, and the same reference numerals are assigned to the same as or similar to the configurations.

Referring to FIG. 11, a plurality of protrusions 620 may be disposed on one surface of the piezoelectric part 1000 facing the user's skin. In detail, the protrusion 620 may be disposed on the other surface of the second base layer 120 facing the user's skin.

The protrusion 620 may include a material harmless to the human body. As an example, the protrusion 620 may include the same maternal as the second base layer 120. The protrusion 620 may be integrally formed with the second base layer 120. The protrusion 620 may be disposed to protrude from the other surface of the second base layer 120 toward the user's skin. The protrusions 620 may be disposed on the other surface of the second base layer 120 in a shape of a plurality of points spaced apart from each other. In addition, the protrusions 620 may be disposed on the other surface of the second base layer 120 in a shape of a plurality of straight lines or curved lines spaced apart from each other. In addition, the protrusion 620 may be disposed on the other surface of the second base layer 120 in at least one line shape. As an example, the protrusion 620 may be disposed on the other surface of the second base layer 120 in at least one spiral shape.

When the user wears the mask 2000, the protrusion 620 may form a predetermined space between the piezoelectric part 1000 and the user's skin. Accordingly, it is possible to prevent cosmetics or drugs between the piezoelectric part 1000 and the skin from being pushed out to an edge region of the piezoelectric part 1000 by the pressure generated when the mask 2000 are worn and/or the ultrasonic energy generated from the piezoelectric element 400. That is, the protrusion 620 may serve as a partition wall preventing cosmetics or drugs from getting out of the piezoelectric part 1000. Therefore, the user may effectively inject cosmetics or drugs into the skin using the mask 2000.

FIG. 12 is a cross-sectional view of an arrangement relationship between a body and a piezoelectric part according to an embodiment.

Referring to FIG. 12, the piezoelectric part 1000 may be disposed on the body 2001. The body 2001 may include a plurality of support members 2100, and the piezoelectric part 1000 may be disposed on the support member 2100.

The support member 2100 may include a first support member 2110, a second support member 2120, and a third support member 2130.

The first support member 2110 may face the user's skin. In detail, an upper surface of the first support member 2110 may be one surface of the above-described mask 2000 and may face the user's skin. The upper surface of the first support member 2110 may be in direct contact with the user's skin.

The first support member 2110 may include a material harmless to the human body. In addition, the first support member 2110 may include a material having softness and elasticity. For example, the first support member 2110 may include at least one material of silicone, a thermoplastic resin, a thermoplastic silicone resin, a thermoplastic elastomer, a polyurethane elastomer, an ethylene vinyl acetate (EVA), a polyvinyl chloride (PVC) in which a harmless plasticizer and a stabilizer are added. Preferably, the first support member 2110 may include a silicone elastomer that is relatively light, may minimize irritation upon contact with the user's skin, and has a predetermined elasticity. In addition, the first support member 2110 may be transparent or colored, but the embodiment is not limited thereto.

The first support member 2110 may include the same material as at least one of the first base layer 110, the second base layer 120, and the protective layer 550 of the piezoelectric part 1000. As an example, when the first base layer 110, the second base layer 120, and the protective layer 550 include the same material, the first support member 2110 may have the same material as the components to have an improved bonding force.

The first support member 2110 may have a first thickness defined as a thickness in the vertical direction (z-axis direction). The first thickness may be about 500 µm to about 1.5 mm. In detail, the first thickness may be about 700 µm to about 1.3 mm. In more detail, the first thickness may be about 800 µm to about 1.2 mm. When the first thickness is less than about 500 µm, elastic deformation characteristics of the first support member 2110 may be deteriorated, and the third support member 2130 described later may not be effectively protected. In addition, when the first thickness exceeds about 1.5 mm, the overall thickness of the body 2001 may increase, and a weight of the mask 2000 may increase. Accordingly, the user wearing the mask 2000 may easily feel fatigue due to the weight of the mask 2000.

Preferably, the first thickness may be 950 µm to 1.05 mm in consideration of elastic deformation characteristics, reliability, and weight of the first support member 2110.

The second support member 2120 may be disposed below the first support member 2110. The second support member 2120 may be disposed outside. A lower surface of the second support member 2120 may be exposed to the outside as the other surface of the mask 2000 described above. The second support member 2120 may be spaced apart from the user's skin.

The second support member 2120 may include a material harmless to the human body. In addition, the second support member 2120 may include a material having softness and elasticity. For example, the second support member 2120 may include at least one material of silicone, a thermoplastic resin, a thermoplastic silicone resin, a thermoplastic elastomer, a polyurethane elastomer, an ethylene vinyl acetate (EVA), a polyvinyl chloride (PVC) in which a harmless plasticizer and a stabilizer are added. Preferably, the second support member 2120 may include a silicone elastomer that is relatively light, may minimize irritation upon contact with the user's skin, and has a predetermined elasticity. In addition, the second support member 2120 may be transparent or colored, but the embodiment is not limited thereto. As an example, the first support member 2110 and the second support member 2120 may be colored so that the third support member 2130 is not visible to the outside.

The second support member 2120 may include the same material as at least one of the first base layer 110, the second base layer 120, and the protective layer 550 of the piezoelectric part 1000. As an example, when the first base layer 110, the second base layer 120, and the protective layer 550 include the same material, the second support member 2120 may include the same material as the components. In addition, the second support member 2120 may include the same material as the first support member 2110. Accordingly, the first support member 2110 and the second support member 2120 may have an improved bonding force with the piezoelectric part 1000.

The second support member 2120 may have a second thickness defined as a thickness in the vertical direction (z-axis direction). The second thickness may be about 500 µm to about 1.5 mm. In detail, the second thickness may be about 700 µm to about 1.3 mm. In more detail, the second thickness may be about 800 µm to about 1.2 mm. When the second thickness is less than about 500 µm, elastic deformation characteristics of the second support member 2120 may be deteriorated, and the third support member 2130 disposed between the first support member 2110 and the second support member 2120 may not be effectively protected. In addition, when the second thickness exceeds about 1.5 mm, the overall thickness of the body 2001 may increase, and the weight of the mask 2000 may increase. Accordingly, the user wearing the mask 2000 may easily feel fatigue due to the weight of the mask 2000. Preferably, the second thickness may be 950 µm to 1.05 mm in consideration of elastic deformation characteristics, reliability, and weight of the second support member 2120. In addition, the thickness (second thickness) of the second support member 2120 may be the same as the thickness (first thickness) of the first support member 2110. Accordingly, the mask 2000 may have improved process efficiency.

The third support member 2130 may be disposed between the first support member 2110 and the second support member 2120. The third support member 2130 may support the first and second support members 2110 and 2120 between the first and second support members 2110 and 2120. An upper surface of the third support member 2130 may face and be in direct contact with a lower surface of the first support member 2110. In addition, a lower surface of the third support member 2130 may face and be in direct contact with an upper surface of the second support member 2120. The first support member 2110 and the second support member 2120 may be disposed to surround the outside of the third support member 2130. As an example, the drawing shows only a cross section of a partial region of the body 2001, but at least one of the first and second support members 2110 and 2120 may be disposed on a side surface of the third support member 2130. Accordingly, the third support member 2130 may not be exposed to the outside by the first and second support members 2110 and 2120.

The third support member 2130 may include a material different from the first support member 2110 and the second support member 2120. In detail, the third support member 2130 may include a material having a higher strength than the first support member 2110 and the second support member 2120. The third support member 2130 may include a metal material. For example, the third support member 2130 may include at least one metal of aluminum (Al), copper (Cu), silver (Ag), gold (Au), platinum (Pt), chromium (Cr), nickel (Ni), molybdenum (Mo), titanium (Ti), tin (Sn), tungsten (W), iron (Fe), and alloys thereof.

The third support member 2130 may have a third thickness defined as a thickness in the vertical direction (z-axis direction). The third thickness may be smaller than the first and second thicknesses. For example, the third thickness may be about 200 μm to about 1.2 mm. In detail, the third thickness may be about 300 μm to 1.1 mm. When the third thickness is less than about 200 μm, it may be difficult for the third support member 2130 to effectively support the first and second support members 2110 and 2120. Accordingly, the reliability of the mask 2000 may be deteriorated, and it may be difficult to maintain a shape of the mask 2000. In addition, when the third thickness exceeds about 1.2 mm, elastic deformation characteristics of the body 2001 may be deteriorated, and a thickness of the body 2001, furthermore, the overall thickness and weight of the mask 2000 may increase. Accordingly, the user wearing the mask 2000 may easily feel fatigue due to the weight of the mask 2000. Preferably, the third thickness may be about 350 μm to about 850 μm in consideration of elastic deformation characteristics, reliability, and weight of the body 2001.

The body 2001 may include a first recess R1. The first recess R1 may be disposed on one surface of the body 2001 facing the user's skin. The first recess R1 may have a concave shape from one surface of the body 2001 toward the other surface, for example, in an outward direction of the body 2001.

The first recess R1 may be formed in a region corresponding to at least one of the first region 2031, the second region 2033, and the third region 2035 of the mask 2000 described above. For example, the first recess R1 on the first region 2031 may be provided in a shape and a plane area corresponding to the user's brow region. In addition, the first recess R1 on the second region 2033 may be provided in a shape and a plane area corresponding to the right eye rim region of the user. In addition, the first recess R1 on the third region 2035 may be provided in a shape and a plane area corresponding to the left eye rim region of the user.

The first recess R1 may be formed on the first support member 2110 and the third support member 2130. The first recess R1 may be formed to pass through the first support member 2110 and the third support member 2130. The upper surface of the second support member 2120 facing the user's skin may be exposed under the first recess R1.

The piezoelectric part 1000 may be disposed in the first recess R1. The piezoelectric part 1000 may have a shape corresponding to the first recess R1. As an example, when viewed in a plane, the piezoelectric part 1000 may have a horizontal width corresponding to the first recess R1. In addition, the piezoelectric part 1000 may have a plane area corresponding to the first recess R1. The piezoelectric part 1000 may be inserted and fixed in the first recess R1. In this case, the first base layer 110 of the piezoelectric part 1000 may face the upper surface of the second support member 2120, and the second base layer 120 may face the user's skin.

A sidewall of the first recess R1 may face a part of a side surface of the piezoelectric part 1000. In detail, a side surface of the first support member 2110 and a side surface of the third support member 2130 that are exposed by the first recess R1 may be in direct contact with a side surface of the piezoelectric part 1000.

The piezoelectric part 1000 may be disposed to be partially or entirely inserted in the first recess R1. For example, when a part of the piezoelectric part 1000 is disposed in the first recess R1, a height of the first recess R1 in the vertical direction (z-axis direction) may be different from a height of the piezoelectric part 1000 in the vertical direction (z-axis direction). In detail, the height of the first recess R1 may be smaller than the height of the piezoelectric part 1000. Accordingly, a part of the piezoelectric part 1000 may be disposed to be inserted in the first recess R1, and the rest of the piezoelectric part 1000 may have a shape protruding from one surface of the body 2001, for example, the upper surface of the first support member 2110 toward the user's skin. In detail, the piezoelectric part 1000 may protrude further toward the user than the one surface on one surface of the body 2001 facing the user's skin. That is, an upper surface of the second base layer 120 may be disposed above the upper surface of the first support member 2110.

In this case, a height of the piezoelectric part 1000 protruding from one surface of the body 2001 may be defined as a first height h1, and the first height h1 may be about 15% to about 85% of the overall thickness (z-axis direction) of the piezoelectric part 1000. In detail, the first height h1 may be about 20% to about 80% of the overall thickness of the piezoelectric part 1000.

When a ratio of the first height h1 to the overall thickness of the piezoelectric part 1000 is less than 15%, when the user wears the mask 2000, the degree to which the piezoelectric part 1000 protrudes from one surface of the body 2001 may be small. In this case, the piezoelectric part 1000 may be spaced apart from the users skin without direct/indirect contact with the user's skin, and thus, it may be difficult to effectively provide ultrasonic energy to the user's skin.

In addition, when the ratio of the first height h1 to the overall thickness of the piezoelectric part 1000 exceeds 85%, the degree to which the piezoelectric part 1000 protrudes from one surface of the body 2001 may be too large. In this case, the piezoelectric part 1000 may be separated from the body 2001 while the user wears or removes the mask 2000 or the ultrasonic energy is emitted from the piezoelectric part 1000.

Therefore, it is preferable that the height (first height h1) of the piezoelectric part 1000 exposed on the body 2001 satisfies the above-described range in consideration of the reliability of the mask 2000 and ultrasonic energy provided to the skin.

An adhesive member 2300 may be disposed between the body 2001 and the piezoelectric part 1000. The adhesive member 2300 may include at least one of acrylic, synthetic rubber, natural rubber, synthetic resin, epoxy, and silicone.

The adhesive member 2300 may be disposed in the first recess R1. The adhesive member 2300 may be disposed on the second support member 2120 exposed under the first recess R1. In detail, the adhesive member 2300 may be disposed on the upper surface of the second support member 2120 exposed by the first recess R1. The piezoelectric part 1000 may be fixed on the body 2001 by the adhesive member 2300.

The adhesive member 2300 may have a shape corresponding to the first recess R1. When viewed in a plane, a plane area of the adhesive member 2300 may be less than or equal to the plane area of the first recess R1. For example, the adhesive member 2300 may be provided in the same plane area as the first recess R1 to improve adhesion between the body 2001 and the piezoelectric part 1000.

A thickness (z-axis direction) of the adhesive member 2300 may be about 20 μm to about 100 μm. In detail, the thickness of the adhesive member 2300 may be about 30 μm to about 70 μm. When the thickness of the adhesive member 2300 is less than about 20 μm, the adhesion between the piezoelectric part 1000 and the body 2001 may be low. In addition, when the thickness of the adhesive member 2300 is about 100 μm, elastic deformation characteristic of the mask 2000 may be deteriorated by the adhesive member 2300. Preferably, the thickness of the adhesive member 2300 may be about 35 μm to about 50 μm in consideration of the adhesion and the elastic deformation characteristics of the mask 2000.

FIGS. 13 to 15 are other cross-sectional views of an arrangement relationship between a body and a piezoelectric part according to an embodiment. In the description using FIGS. 13 to 15, descriptions of configurations the same as or similar to those of the above-described mask are omitted, and the same reference numerals are assigned to the same as or similar to the configurations.

First, referring to FIG. 13, the body 2001 may include a first recess R1. The first recess R1 may be disposed on one surface of the body 2001 facing the user's skin. The first recess R1 may have a concave shape from one surface of the body 2001 toward the other surface of the body 2001.

The first recess R1 may be formed on the first support member 2110. The first recess R1 may be formed to pass through the first support member 2110. The upper surface of the third support member 2130 facing the user's skin may be exposed under the first recess R1.

The piezoelectric part 1000 may be disposed in the first recess R1. In this case, the first base layer 110 of the piezoelectric part 1000 may face the upper surface of the third support member 2130, and the second base layer 120 may face the user's skin. In addition, the side surface of the first recess R1 may face a part of the side surface of the piezoelectric part 1000. In detail, the side surface of the first support member 2110 exposed by the first recess R1 may be in direct contact with the side surface of the piezoelectric part 1000.

An adhesive member 2300 may be disposed between the body 2001 and the piezoelectric part 1000. The adhesive member 2300 may be disposed in the first recess R1. The adhesive member 2300 may be disposed on the third support member 2130 exposed under the first recess R1. In detail, the adhesive member 2300 may be disposed on the upper surface of the third support member 2130 exposed by the first recess R1. The piezoelectric part 1000 may be fixed on the body 2001 by the adhesive member 2300.

Referring to FIG. 14, the body 2001 may include a first recess R1 formed on the first support member 2110. The piezoelectric part 1000 may be disposed in the first recess R1. In this case, the first base layer 110 of the piezoelectric part 1000 may face the upper surface of the second support member 2120, and the second base layer 120 may face the user's skin. The piezoelectric part 1000 may be fixed on the body 2001 by the adhesive member 2300. In detail, the adhesive member 2300 may be disposed on the upper surface of the third support member 2130 exposed by the first recess R1, and the piezoelectric part 1000 may be fixed on the body 2001 by the third support member 2130.

In addition, the body 2001 may include a second recess R2. The second recess R2 may be formed in the first recess R1. The second recess R2 may have a concave shape from one surface of the body 2001 toward the other surface of the body 2001.

The second recess R2 may be formed on the third support member 2130. In detail, the second recess R2 may be formed on the third support member 2130 and the adhesive member 2300. The second recess R2 may be formed to pass through the third support member 2130 and the adhesive member 2300. That is, a height h2 of the second recess R2 may correspond to a sum of a thickness of the third support member 2130 and the thickness of the adhesive member 2300. Accordingly, the upper surface of the second support member 2120 may be exposed under the second recess R2.

The second recess R2 may have a planar shape corresponding to the piezoelectric element 400. In addition, the second recess R2 may be formed in a region corresponding to the piezoelectric part 1000. In detail, the second recess R2 may be disposed in a region overlapping the piezoelectric element 400 in the vertical direction. In more detail, a center of the second recess R2 may overlap a center of the piezoelectric element 400 in the vertical direction.

A horizontal width d2 of the second recess R2 may be smaller than that of the first recess R1. In detail, the horizontal width d2 of the second recess R2 may be the same as or different from a horizontal width of the piezoelectric element 400. For example, when the planar shape of the piezoelectric element 400 and the second recess R2 is circular, a diameter d2 of the second recess R2 may be about 40% to 160% of a diameter of the piezoelectric element 400. In detail, a diameter d2 of the second recess R2 may be 50% to 150% of the diameter of the piezoelectric element.

As the diameter d2 of the second recess R2 satisfies the above-described range, wave energy emitted from the piezoelectric element 400 may be more effectively reflected in an upper direction, for example, toward the second base layer 120. Accordingly, the mask 2000 according to the embodiment may further minimize loss of ultrasonic energy emitted from the piezoelectric part 1000 and may effectively provide the ultrasonic energy to the user's skin.

Referring to FIG. 15, the body 2001 may include a plurality of support members 2100, and the piezoelectric part 1000 may be disposed on the support member 2100.

The support member 2100 may further include a fourth support member 2140 in addition to the first to third support members 2110, 2120, and 2130 described above.

The fourth support member 2140 may be disposed between the first support member 2110 and the third support member 2130. The fourth support member 2140 may be disposed closer to the first support member 2110 than the second support member 2120. The fourth support member 2140 may be disposed on a lower surface of the first support member 2110.

The fourth support member 2140 may support the first and second support members 2110 and 2120 between the first and second support members 2110 and 2120. The fourth support member 2140 may include a material having a higher strength than the first and second support members 2110 and 2120. For example, the fourth support member 2140 may include a metal material. In detail, the fourth support member 2140 may include at least one metal of aluminum (Al), copper (Cu), silver (Ag), gold (Au), platinum (Pt), chromium (Cr), nickel (Ni), molybdenum (Mo), titanium (Ti), tin (Sn), tungsten (W), iron (Fe), and alloys thereof.

A thickness of the fourth support member 2140 may be smaller than the thickness of each of the first and second support members 2110 and 2120. For example, the thickness of the fourth support member 2140 may be about 200 μm to about 1.2 mm. In detail, the thickness of the fourth support member 2140 may be about 300 μm to 1.1 mm. Preferably, the thickness of the fourth support member 2140 may be about 350 μm to about 850 μm in consideration of the elastic deformation characteristics, reliability, weight of the body 2001. In addition, the thickness of the fourth support member 2140 may be provided equal to the thickness of the third support member 2130. Accordingly, the mask 2000 may have improved process efficiency.

The body 2001 may include a first recess R1. The first recess R1 may be disposed on one surface of the body 2001 facing the user's skin. The first recess R1 may have a concave shape from one surface of the body 2001 toward the other surface of the body 2001.

The first recess R1 may be formed on the first support member 2110 and the fourth support member 2140. The first recess R1 may be formed to pass through the first support member 2110 and the fourth support member 2140. The upper surface of the third support member 2130 may be exposed under the first recess R1.

The piezoelectric part 1000 may be disposed in the first recess R1. In this case, the first base layer 110 of the piezoelectric part 1000 may face the upper surface of the third support member 2130, and the second base layer 120 may face the user's skin. In addition, the side surface of the first recess R1 may face a part of the side surface the side surface of the piezoelectric part 1000. In detail, the side surface of the first support member 2110 exposed by the first recess R1 and a side surface of the fourth support member may be in direct contact with the side surface of the piezoelectric part 1000.

An adhesive member 2300 may be disposed between the plurality of support members 2100. The adhesive member 2300 may include at least one of acrylic, synthetic rubber, natural rubber, synthetic resin, epoxy, and silicone.

The adhesive member 2300 may include a first adhesive member 2310 disposed between the body 2001 and the piezoelectric part 1000. The first adhesive member 2310 may be disposed in the first recess R1. The first adhesive member 2310 may be disposed on the third support member 2130 exposed under the first recess R1. In detail, the first adhesive member 2310 may be disposed on the upper surface of the third support member 2130 exposed by the first recess R1. Accordingly, the piezoelectric part 1000 may be fixed on the body by the first adhesive member 2310. In addition, the first adhesive member 2310 may be disposed between the third support member 2130 and the fourth support member 2140. Accordingly, the first adhesive member 2310 may adhere the third support member 2130 and the fourth support member 2140 to each other.

The adhesive member 2300 may include a second adhesive member 2320 disposed between the first support member 2110 and the fourth support member 2140. The second adhesive member 2320 may adhere the first support member 2110 and the fourth support member 2140 to each other. In addition, a side surface of the second adhesive member 2320 exposed by the first recess R1 may be in direct contact with the side surface of the piezoelectric part 1000. Therefore, the piezoelectric part 1000 may be more stably coupled to the body 2001. In detail, the first adhesive member 2310 and the second adhesive member 2320 are respectively disposed on the side surface and the lower surface of the piezoelectric part 1000, so that the piezoelectric part 1000 may have improved adhesion on the body 2001.

In addition, the body 2001 may include a second recess R2. The second recess R2 may be formed in the first recess R1. The second recess R2 may have a concave shape from one surface of the body 2001 toward the other surface of the body 2001.

The second recess R2 may be formed on the third support member 2130. In detail, the second recess R2 may be formed on the third support member 2130 and the adhesive member 2300. The second recess R2 may be formed to pass through the third support member 2130 and the adhesive member 2300. The upper surface of the second support member 2120 may be exposed under the second recess R2.

The second recess R2 may have a planar shape corresponding to the piezoelectric element 400. In addition, the second recess R2 may be formed in a region corresponding to the piezoelectric part 1000. In detail, the second recess R2 may be disposed in a region overlapping the piezoelectric element 400 in the vertical direction.

A horizontal width of the second recess R2 may be smaller than that of the first recess R1. In detail, the horizontal width of the second recess R2 may be the same as or different from a horizontal width of the piezoelectric element 400. For example, when the planar shape of the piezoelectric element 400 and the second recess R2 is circular, a diameter of the second recess R2 may be about 40% to about 160% of a diameter of the piezoelectric element 400. In detail, the diameter of the second recess R2 may be 50% to 150% of the diameter of the piezoelectric element.

FIG. 16 is a front view of a user wearing a mask according to an embodiment, and FIG. 17 is a rear view of the user wearing the mask according to the embodiment. In addition, FIG. 18 is a view showing an arrangement relationship between a mask and skin according to an embodiment.

Referring to 16 to 18, a user 15 may wear the mask 2000. For example, the user may place the opening 2010 of the mask 2000 at a position corresponding to both eyes of the user, and the bending portion 2020 of the mask 2000 may be mounted on the nose to set a position of the mask 2000. Thereafter, the user may fix the mask 2000 on the face of the user through the extension portion 2050 and/or the fixing member 2070.

Accordingly, the first to third regions 2031, 2033, and 2035 of the mask 2000 may be disposed to correspond to the blow, right eye rim, and left eye rim regions of the user 15, respectively. In addition, the piezoelectric part 1000 according to the embodiment may be disposed on the first to third regions 2031, 2033, and 2035, and the piezoelectric part 1000 may be disposed to face the blow, right eye rim, and left eye rim regions of the user 15. In this case, the piezoelectric part 1000 may be in direct contact with a skin 15 of the blow, right eye rim, and left eye rim regions of the user 10 and may be in indirect contact with the skin 15 by cosmetics or drugs between the piezoelectric part 1000 and the skin 15.

In addition, the mask 2000 according to the embodiment may include a power supply unit (not shown). The power supply unit may be disposed outside the mask 2000. For example, the power supply unit may be provided in a form of a terminal on the other surface of the mask 2000. The mask 2000 may receive power by connecting an external power cable or the like to the power supply unit.

The mask 2000 may be operated by applied power. For example, the piezoelectric part 1000 may generate ultrasonic energy to power applied through the power supply unit. The ultrasonic energy of the piezoelectric part 1000 may cause cracks in the stratum corneum of the skin 15 of the user 15 to form a fine perforation and may effectively absorb cosmetics or drugs between the mask 2000 and the skin 15 of the user 15.

In addition, the mask 2000 may include a deformable member (not shown). The deformable member may be disposed on one surface of the mask 2000 facing the skin 15 of the user 15. The deformable member may be disposed in a region other than the first to third areas 2031, 2033, and 2035.

The deformable member may include a material of which shape is changed by external pressure. As an example, the deformable member may include a material such as an air gap or a sponge, but the embodiment is not limited thereto, and may include various materials of which shape is changed by external pressure. Accordingly, when the user 15 wears the mask 2000, the deformable member may be deformed into a shape corresponding to a face shape of the user 15. Therefore, the mask 2000 and the skin 15 of the user 15 may be effectively adhered to each other. In addition, when a plurality of users wear the mask 2000, the deformable member may be deformed to correspond to each face shape, so that the skin 15 of the user 15 and the mask 2000 may be effectively adhered to each other.

That is, the mask 2000 according to the embodiment may be effectively adhered to the skin 15 of the user 15. In detail, the body 2001 of the mask 2000 and the piezoelectric part 1000 on the body 2001 may be elastically deformed to correspond to a shape of the skin 15 of the user 15. In addition, the piezoelectric part 1000 may include a plurality of piezoelectric elements 400 to provide uniform ultrasonic energy to a skin region corresponding to the piezoelectric part 1000. Accordingly, the mask 2000 may maximize the supply of cosmetics or drugs to a region where wrinkles are relatively easy to occur, a region where a stratum corneum is easily formed, and a region where effective supply of cosmetics or drugs is required of the skin of the user 15, it is possible to effectively care or treatment the skin 15 of the user 15 in a short time.

Hereinafter, a skin care device including a mask according to an embodiment will be described with reference to FIGS. 19 to 25.

Referring to FIGS. 19 and 20, a skin care device 1 according to an embodiment may include a mask 2000 and a controller 3000.

The mask 2000 according to the embodiment may include a first terminal part 2090. The first terminal part 2090 may be disposed on the other surface of the mask 2000. In detail, the first terminal part 2090 may be disposed on an outer surface of the body 2001. The first terminal part 2090 may be spaced apart from the piezoelectric region 2030. As an example, the first terminal part 2090 may be disposed on a relatively flat region, for example, on a region corresponding to a user's temple.

The first terminal part 2090 may be electrically connected to the piezoelectric part 1000 and may be connected to a terminal part (a second terminal part 3330) of the controller 3000 described later. The first terminal part 2090 may provide an electric signal, a control signal, a power signal, and the like that are applied from the controller 3000 to the piezoelectric part 1000 of the mask 2000. In detail, the first to third piezoelectric parts 1000a, 1000b, and 1000c may provide the same or different ultrasonic energy to the user's skin by a signal applied from the controller 3000.

The controller 3000 may be connected to the mask 2000. The controller 3000 may be physically and electrically connected to the mask 2000. The controller 3000 may provide a control signal, power, and the like to the mask 2000.

The controller 3000 may include a body 3100. The body 3100 may have a predetermined strength and may include a material harmless to the human body. For example, the body 3100 may include at least one material of plastic, polypropylene (PP), polyethylene (PE), polycarbonate (PC), polybutylene terephthalate (PBT), acrylonitrile butadiene styrene copolymer (ABS), poly oxy methylene, polyacetal (POM), polyphenylene oxide (PPO) resin, and a modified PPO resin. In addition, the body 3100 may include glass or metal. As an example, the body 3100 may include at least one of silver (Ag), chromium (Cr), molybdenum (Mo), nickel (Ni), aluminum (Al), stainless steel, and alloys thereof.

The controller 3000 may include a connection portion. The connection portion may be disposed between the body 3100 of the controller 3000 and the mask 2000 and may connect the body 3100 and the body 2001 of the mask 2000.

The connection portion may include a connection wire 3310 and the second terminal part 3330. The connection wire 3310 may be disposed between the body 3100 and the second terminal part 3330. For example, one end of the connection wire 3310 may be connected to the body 3100 of the controller 3000, and the other end opposite to one end of the connection wire 3310 may be connected to the second terminal part 3330. The connection wire 3310 may be electrically connected to components disposed in an accommodation space of the body 3100. The connection wire 3310 may be a wire connecting an electrical signal, power, and the like between the controller 3000 and the mask 2000.

The second terminal part 3330 of the controller 3000 may have a shape corresponding to the first terminal part 2090 and may be connected to the first terminal part 2090 of the mask 2000. The second terminal part 3330 may be physically and electrically connected to the first terminal part 2090. The controller 3000 may provide the control signal to the piezoelectric part 1000 of the mask 2000 through the first terminal part 2090 and the second terminal part 3330.

The body 3100 may include the accommodation space (not shown) therein. A circuit board (not shown), a power supply unit (not shown), and the like may be disposed in the accommodation space of the body 3100.

The circuit board may include at least one of a printed circuit board (PCB) made of a resin material, a metal core PCB (MCPCB), a nonflexible PCB, a flexible PCB (FPCB), and a ceramic material. The circuit board may include a layer of resin material or a ceramic-based layer, and the resin material may be formed of a silicone, an epoxy resin, a thermosetting resin including a plastic material, or a highly heat resistant or highly light resistant material. The ceramic material may include low temperature cofired ceramic (LTCC) or high temperature cofired ceramic (HTCC) that is simultaneously fired. At least one control element for controlling the mask 2000 and the controller 3000 may be disposed on the circuit board.

The power supply unit may supply power to the skin care device 1. For example, the power supply unit may supply power to each of the controller 3000 and the mask 2000. The power supply unit may include a battery. The battery may include at least one selected from a primary battery such as a manganese (Mn) battery, an alkaline battery, a mercury battery, a silver oxide battery, and the like. In addition, the battery may include at least one selected from a secondary battery such as a nickel cadmium (Ni—Cd) battery, a nickel hydrogen (Ni-MH) battery, and a lithium ion (Li-ion) battery, and the like.

When the power supply unit of the skin care device 1 includes a rechargeable secondary battery, a charging terminal part (not shown) for charging may be disposed outside the body 3100. The charging terminal part may be electrically connected to the power supply unit disposed inside the body 3100, and a part of the charging terminal part may be exposed outside the body 3100. The user may charge the battery by connecting a charging cable, a USB cable, or the like to the charging terminal part exposed to the outside of the body 3100.

A button part 3200 may be disposed outside the body 3100. The button part 3200 may include at least one physical button for controlling power, operation, intensity, and the like of the skin care device 1. In addition, the button part 3200 may include an electric button on which the touch electrode or the like is formed. The user may control the power, operation mode, and operation intensity of the skin care device 1 through the button part 3200.

The button part 3200 may be provided outside the body 3100 in plural. For example, the button part 3200 may include a first button 3211, a second button 3212, and a third button 3213 disposed in a front region of the body 3100. The first button 3211 may be a switch for selecting the first piezoelectric part 1000*a*, the second button 3212 may be a switch for selecting the second piezoelectric part 1000*b*, and the third button 3213 may be a switch for selecting the third piezoelectric part 1000*c*. In addition, the button part 3200 may include a fourth button 3214 disposed in the front region of the body 3100. The fourth button 3214 may be a switch for selecting all of the first to third piezoelectric parts 1000*a*, 1000*b*, and 1000*c* at once.

The button part 3200 may include an operation button 3230 and a stop button 3240 disposed in the front region of the body 3100. The operation button 3230 may be a switch for starting the operation of the piezoelectric part selected by the first to fourth buttons 3211, 3212, 3213, and 3214. In addition, the stop button 3240 may be a switch for stopping or temporarily stopping the operation of the piezoelectric parts 1000*a*, 1000*b*, and 1000*c* in operation.

The button part 3200 may include control buttons 3221 and 3222. The control buttons 3221 and 3222 may be disposed in a side region of the body 3100. The control button may include an upper control button 3221 and a lower control button 3222. The control buttons 3221 and 3222 may adjust operation intensity of the piezoelectric part 1000 within a set range.

A display part 3300 may be disposed outside the body 3100. The display part 3300 may display a state of the skin care device 1. For example, the display part 3300 may display a connection state, an operation mode, a power state, and the like of the skin care device 1. For example, the display part 3300 may include displays such as LCD, LED, OLED, and QD to provide information to the user. In addition, the display part 3300 may include an indicator lamp. The indicator lamp may provide information to the user through emission color, emission time, and the like. For example, when the user operates the skin care device 1 through the button part 3200, the indicator lamp may emit light with a set color. In addition, the indicator lamp may emit light in various colors depending on a piezoelectric part operating among the first to third piezoelectric parts 1000*a*, 1000*b*, and 1000*c*. In addition, the indicator lamp may emit light in various colors according to the operation intensity of the piezoelectric part 1000. Accordingly, the display part 3300 may effectively provide information on the state of the skin care device 1 to the user.

A speaker (not shown) may be disposed in the accommodation space of the body 3100. The speaker may output information about a state of the skin care device 1, for example, a power state, an operation state, and the like, by sound. For example, when the user operates the skin care device 1, the speaker may output a sound for the start of the operation, and when the user stops the operation of the skin care device 1 or a set time of the skin care device 1 ends, the speaker may output a sound for the end of the operation.

FIG. 21 is a flowchart showing an operation of a skin care device according to an embodiment, and FIG. 22 is a block diagram showing a configuration of a skin care device according to an embodiment. In addition, FIGS. 23 to 25 are views showing a method of operating first to third piezoelectric parts according to an embodiment.

First, a method of operating the skin care device 1 according to an embodiment will be described with reference to FIG. 21.

The method of operating of the skin care device 1 may include supplying power to the skin care device 1. The supplying of power may be an operation of supplying power to the mask 2000 and the controller 3000 under control of the user. In detail, the supplying of power may be an operation of turning on the power of the skin care device 1 by the user. For example, the user may control the power of the skin care device 1 through a separate power switch or the operation button 3230 disposed on the controller 3000.

In addition, the method of operating of the skin care device 1 may include selecting a region and an intensity. The selecting of the region and intensity may be an operation in which the user selects a region to which ultrasonic energy is applied and selects an intensity of the applied ultrasonic energy. For example, in the operation, the user may select one or more of the first to fourth buttons 3211, 3212, 3213, and 3214 to select a piezoelectric part to be driven. Thereafter, the user may select an intensity of ultrasonic energy emitted from the selected piezoelectric part by using the control buttons 3221 and 3222.

As an example, in the operation, the user may select the first piezoelectric part 1000*a* corresponding to the user's brow region through the first button 3211. In addition, in the operation, the user may select an intensity of ultrasonic energy emitted from the first piezoelectric part 1000*a* through the control buttons 3221 and 3222 of the controller 3000. In this case, information on a region and intensity set by the user may be provided on the display part 3300.

As another example, in the operation of selecting the region and the intensity, the user may select the second piezoelectric part 1000*b* corresponding to the user's right eye rim through the second button 3212 of the controller 3000 and may select the third piezoelectric part 1000*c* corresponding to the user's right eye rim through the third button 3213. In addition, in the operation, the user may select an intensity of ultrasonic energy emitted from each of the second piezoelectric part 1000b or the third piezoelectric part 1000c selected through the control buttons 3221 and 3222 of the controller 3000. In this case, information on the region and intensity set by the user may be provided on the display part 3300.

As still another example, in the operation of selecting the region and intensity, the user may select the first to third piezoelectric parts 1000a, 1000b, and 1000c corresponding to the user's blow, right eye rim, and left eye rim through the fourth button 3214 of the controller 3000. In addition, in the operation, the user may select the intensity of ultrasonic energy emitted from each of the first to third piezoelectric parts 1000a, 1000b, and 1000c through the control buttons 3221 and 3222 of the controller 3000. In this case, information on the region and intensity set by the user may be provided on the display part.

In addition, the method of operating the skin care device 1 may include an operation of operating. The operation of operating may be an operation of operating in the region and intensity selected in the operation of selecting the region and intensity. For example, the operation of operating may be an operation of operating the mask 2000 through the operation button 3230 after the user selects at least one of the first to fourth buttons 3211, 3212, 3213, and 3214. That is, the operating of operating may be an operation of providing ultrasonic energy to the user's skin.

Thereafter, the skin care device 1 may automatically end the operation after the operation for the set time. In addition, the skin care device 1 may be temporarily stopped or terminated under the user's control during the operation for the set time. For example, the user may temporarily stop or terminate the operation of the mask 2000 through the stop button 3240 during the operation of the skin care device 1.

That is, the skin care device 1 according to the embodiment may effectively provide the ultrasonic energy to the user's skin. For example, the user may selectively provide the ultrasonic energy to the user's skin through the skin care device 1. In detail, the user may select a region where the ultrasonic energy is provided through the first to fourth buttons 3211, 3212, 3213, and 3214 and may set the intensity of ultrasonic energy provided through the control buttons 3221 and 3222.

In addition, the skin care device 1 according to the embodiment may provide different ultrasonic energy depending on the region to minimize stimulation of a relatively sensitive skin region. In detail, the first piezoelectric part 1000a corresponding to the user's brow region may provide ultrasonic energy greater than those of the second and third piezoelectric parts 1000b and 1000c corresponding to both eye rim regions that are relatively sensitive to stimulation.

As an example, each of the first to third piezoelectric parts 1000a, 1000b, and 1000c may be divided into ten levels of operation intensity by the control buttons 3221 and 3222. In this case, the operation intensity of each operation of the first piezoelectric part 1000a may be greater than the operation intensity of each operation of the second and third piezoelectric parts 1000b and 1000c corresponding thereto.

That is, ultrasonic energy having an intensity smaller than that of the first piezoelectric part 1000a is provided to the second and third piezoelectric parts 1000b and 1000c corresponding to the skin region that is relatively sensitive to stimulation, thereby minimizing the user's skin stimulation and providing optimal ultrasonic energy.

In addition, the skin care device 1 according to the embodiment may provide uniform ultrasonic energy to the user's skin.

Referring to FIG. 22, the controller 3000 may include a microcontroller unit (MCU) 3010 and a switch unit 3030. The microcontroller unit 3010 and the switch unit 3030 may be connected to the piezoelectric part 1000 and may control the operation of the piezoelectric part 1000.

The microcontroller unit 3010 may receive information input from the button part 3200. The microcontroller unit 3010 may generate a driving signal corresponding thereto in response to the received information. The microcontroller unit 3010 may control an operation of the switch unit 3030 and may control input waveforms applied to the plurality of piezoelectric parts 1000. For example, the microcontroller unit 3010 may control a voltage, a frequency, a pulse width, and the like applied to each of the plurality of piezoelectric parts 1000.

The switch unit 3030 may be disposed between the microcontroller unit 3010 and the piezoelectric part 1000. The switch unit 3030 may include a switch. For example, the switch unit 3030 may include one or a plurality of switches selected from single pole single throw (SPST), single pole dual throw (SPDT), dual poles single throw (DPST), dual poles dual throw (DPDT), reversing DPDT, and three and more (multi) poles single throw)), and multi poles dual throw (MPDT).

The switch unit 3030 may control ON/OFF of the first to third piezoelectric parts 1000a, 1000b, and 1000c based on a control signal applied from the microcontroller unit 3010.

As an example, in the operation of selecting the region and intensity, the user may select one of the first to third buttons 3211, 3212, and 3213. For example, the user may select only the first button 3211 as shown in FIG. 7. In this case, the switch unit 3030 may switch the first piezoelectric part 1000a to an ON state and may switch the second piezoelectric part 1000b and the third piezoelectric part 1000b and 1000c to an OFF state. Accordingly, the first piezoelectric part 1000a may be provided with at least one operation waveform of a voltage of the intensity set by the user, a frequency, and a pulse width.

In this case, the first piezoelectric part 1000a may operate while repeating ON and OFF as shown in FIG. 23A. In detail, the first piezoelectric part 1000a may operate for an operating time OT set by the switch unit 3030 to emit ultrasonic energy and may stop the operation for a waiting time WT set after the operating time OT is terminated. In addition, the first piezoelectric part 1000a may repeat a process of operating again during the operating time OT after the waiting time WT and stopping the operation again during the waiting time WT. The first piezoelectric part 1000a may repeat the process until the set time of the skin care device 1 or an end time by the user.

The operating time OT and the waiting time WT may be the same or different from each other. In addition, the waiting time WT may be a very short time. In detail, the waiting time WT may be a time that the user may not recognize. For example, the waiting time WT may be several milliseconds (ms) to several tens of milliseconds. Accordingly, the user using the skin care device 1 may recognize that ultrasonic energy is continuously provided to the skin region corresponding to the first piezoelectric part 1000a.

In addition, the first piezoelectric part 1000a may maintain an ON state as shown in FIG. 23B. For example, the first piezoelectric part 1000a may maintain the ON state until a set time of the skin care device 1 or a forced termination time of the user by the switch unit 3030.

As another example, in the operation of selecting the region and intensity, the user may select two switches among the first to third buttons 3211, 3212, and 3213. For example, the user may select the first button 3211 and the third button 3213 as shown in FIG. 8. In this case, the switch unit 3030 may switch the first piezoelectric part 1000a and the third button 3213 to an ON state and may switch the second piezoelectric part 1000b to an OFF state. Accordingly, an operation waveform such as a voltage of the intensity set by the user, a frequency, and a pulse width may be provided to each of the first piezoelectric part 1000a and the third piezoelectric part 1000c.

In this case, the first piezoelectric part 1000a and the third piezoelectric part 1000c may operate w % bile repeating ON and OFF as shown in FIG. 24. In detail, the first piezoelectric part 1000a may operate for a first operating time OT1 set by the switch unit 3030 to emit ultrasonic energy and may stop the operation for a first waiting time WT1 set after the first operating time OT1 is terminated. In addition, the first piezoelectric part 1000a may repeat a process of operating again during the first operating time OT1 after the first waiting time WT1 and stopping the operation again during the first waiting time WT1.

In addition, the third piezoelectric part 1000c may operate for a third operating time OT3 set by the switch unit 3030 to emit ultrasonic energy and may stop the operation for a third waiting time WT3 set after the third operating time OT3 is terminated. In addition, the third piezoelectric part 1000c may repeat a process of operating again during the third operating time OT3 after the third waiting time WT3 and stopping the operation again during the third waiting time WT3.

In this case, the first piezoelectric part 1000a and the third piezoelectric part 1000c may be driven individually. For example, the first piezoelectric part 1000a and the third piezoelectric part 1000c may not be driven simultaneously by the switch unit 3030, but may operate at different times, respectively. In detail, the first piezoelectric part 1000a may operate during the third waiting time WT3 of the third piezoelectric part 1000c, and the third piezoelectric part 1000c may operate during the first waiting time WT1 of the first piezoelectric part 1000a.

That is, the first piezoelectric part 1000a and the third piezoelectric part 1000c may operate in a time region overlapping the waiting time of other piezoelectric parts by the switch unit 3030. The first piezoelectric part 1000a and the third piezoelectric part 1000c may repeat the process until a set time of the skin care device 1 or a forced termination time of the user.

The first operating time OT1 and the first waiting time WT1 may be the same or different from each other. The third operating time OT3 and the third waiting time WT3 may be the same or different from each other. In addition, the first operating time OT1 may be shorter than or equal to the third waiting time WT3, and the third operating time OT3 may be shorter or equal to the first waiting time WT1.

The first waiting time WT1 and the third waiting time WT3 may be very short. In detail, the first waiting time WT1 and the third waiting time WT3 may be times that the user may not recognize. For example, the first waiting time WT1 and the third waiting time WT3 may be several milliseconds (ms) to several tens of milliseconds. Accordingly, the user using the skin care device 1 may recognize that ultrasonic energy is continuously provided to the skin regions corresponding to the first piezoelectric part 1000a and the third piezoelectric part 1000c.

That is, the skin care device 1 according to the embodiment may apply an optimal input waveform to each of the piezoelectric parts 1000 selected by the user. In detail, the skin care device 1 may independently control each of the piezoelectric parts 1000a and 1000c selected by a simple structure including one transmission path (TX path) disposed between the microcontroller unit 3010 and the switch unit 3030.

Accordingly, the piezoelectric parts 1000a and 1000c may be provided with operation waveforms, such as voltages, frequencies, and pulse widths, which are the same or different from each other. Accordingly, the piezoelectric parts 1000a and 1000c may effectively care or treat the skin and minimize skin stimulation by providing optimal ultrasonic energy to the user's skin.

As still another example, in the operation of selecting the region and intensity, the user may select all of the first to third buttons 3211, 3212, and 3213 as shown in FIG. 25 or select the fourth button 3214. In this case, the switch unit 3030 may switch the first to third piezoelectric parts 1000a, 10b, and 1000c to an ON state. Accordingly, each of the first to third piezoelectric parts 1000a, 1000b, and 1000c may be provided with an operation waveform such as a voltage of an intensity set by the user, a frequency, and a pulse width.

In this case, the first to third piezoelectric parts 1000a, 1000b, and 1000c may operate while repeating ON and OFF as shown in FIG. 9. In detail, the first piezoelectric part 1000a may be operated for the first operating time OT1 set by the switch unit 3030 to emit ultrasonic energy and may stop the operation for the first waiting time WT1 set after the first operating time OT1 is terminated. In addition, the first piezoelectric part 1000a may repeat a process of operating again during the first operating time OT1 after the first waiting time WT1 and stopping the operation again during the first waiting time WT1.

In addition, the second piezoelectric part 1000b may operate for a set second operating time OT2 set by the switch unit 3030 to emit ultrasonic energy and may stop the operation for a second waiting time WT2 set after the second operating time OT2 is terminated. In addition, the second piezoelectric part 1000b may repeat a process of operating again during the second operating time OT2 after the second waiting time WT2 and stopping the operation again during the second waiting time WT2.

In addition, the third piezoelectric part 1000c May Operate for a third Operating time OT3 set by the switch unit 3030 to emit ultrasonic energy and may stop the operation for a third waiting time WT3 set after the third operating time OT3 is terminated. In addition, the third piezoelectric part 1000c may repeat a process of operating again during the third operating time OT3 after the third waiting time WT3 and stopping the operation again during the third waiting time WT3.

In this case, the first to third piezoelectric parts 1000a, 1000b, and 1000c may be driven individually. For example, the first to third piezoelectric parts 1000a, 1000b, and 1000c may not be driven simultaneously by the switch unit 3030, but may operate at different times, respectively.

In addition, the piezoelectric part 1000 may operate with an order set by the switch unit 3030 as one cycle. For example, the piezoelectric part 1000 may repeatedly operate for a set time with an order of the first piezoelectric part 1000a, the second piezoelectric part 1000b, and the third piezoelectric part 1000c as one cycle.

The first piezoelectric part 1000a may operate in a time domain overlapping the second waiting time WT2 and the third waiting time WT3. That is, the first operating time OT1 of the first piezoelectric part 1000*a* may overlap the second and third waiting times WT2 and WT3 in the time domain. In addition, the second piezoelectric part 1000*b* may operate in a time domain overlapping the first waiting time WT1 and the third waiting time WT3. That is, the second operating time OT2 of the second piezoelectric part 1000*b* may overlap the first and third waiting times WT1 and WT3 in the time domain. In addition, the third piezoelectric part 1000*c* may operate in a time domain overlapping the first waiting time WT1 and the second waiting time WT2. That is, the third operating time OT3 of the third piezoelectric part 1000*c* may overlap the first and second waiting times WT1 and WT2 in the time domain.

In summary, each of the first to third piezoelectric parts 1000*a*, 1000*b*, and 1000*c* may operate in a time domain overlapping the waiting time of other piezoelectric parts by the switch unit 3030. The first to third piezoelectric parts 1000*a*, 1000*b*, and 1000*c* may repeat the process until a set time of the skin care device 1 or a forced termination time of the user.

The first operating time OT1 may be shorter than or equal to the first waiting time WT1. The second operating time OT2 may be shorter than or equal to the second waiting time WT2. The third operating time OT3 may be shorter than or equal to the third waiting time WT3. Preferably, the first to third operation times OT1, OT2, and OT3 may be shorter than the corresponding first to third waiting times WT1, WT2, and WT3, respectively, for optimal input waveform application.

In addition, the first operating time OT1 may be shorter than the second waiting time WT2 and the third waiting time WT3. The second operating time OT2 may be shorter than the first waiting time WT1 and the third waiting time WT3. The third operating time OT3 may be shorter than the first waiting time WT1 and the second waiting time WT2.

In addition, the first waiting time WT1 may correspond to a sum of the second operating time OT2 and the third operating time OT3. The second waiting time WT2 may correspond to a sum of the first operating time OT1 and the third operating time OT3. The third waiting time WT3 may correspond to a sum of the first operating time OT1 and the second operating time OT2. That is, the waiting time of the selected one piezoelectric part among the plurality of piezoelectric parts 1000 may correspond to a sum of operation times of the remaining piezoelectric parts in order to optimize the input waveform applied to the piezoelectric part.

In addition, the first to third waiting times WT1, WT2, WT3 may be the same as each other in order to apply the optimal input waveform to each of the plurality of piezoelectric parts 1000, and the first to third operation times OT1, OT2, and OT3 may be the same as each other.

The first waiting time WT1, the second waiting time WT2, and the third waiting time WT3 may be very short. In detail, each of the first to third waiting times WT1, WT2, and WT3 may be times that the user may not recognize. For example, each of the first to third waiting times WT1, WT2, and WT3 may be several milliseconds (ms) to several tens of milliseconds. Accordingly, the user using the skin care device 1 may recognize that ultrasonic energy is continuously provided to the skin regions corresponding to the first to third piezoelectric parts 1000*a*, 1000*b*, and 1000*c*, respectively.

That is, the skin care device 1 according to the embodiment may apply the optimal input waveform to each of the piezoelectric parts 1000 selected by the user. In detail, the skin care device 1 may independently control each of the piezoelectric parts 1000*a*. 1000*b*, and 1000*c* selected by a simple structure including one transmission path (TX path) disposed between the microcontroller unit 3010 and the switch unit 3030.

Accordingly, it is possible to control operation waveforms such as a voltage, a frequency, and a pulse width applied to each of the piezoelectric parts 1000*a*. 1000*b*, and 1000*c*. In detail, the same or different operation waveforms may be provided to each of the piezoelectric parts 1000*a*, 1000*b*, and 1000*c*.

As another example, some of the piezoelectric parts 1000*a*, 1000*b*, and 1000*c* may be provided with the same operation waveform, and the remaining piezoelectric parts may be provided with different operation waveforms. For example, the same operation waveforms may be provided to the second and third piezoelectric parts 1000*b* and 1000*c* corresponding to both eye rim regions that are relatively sensitive to stimulation. On the other hand, an operation waveform stronger than those of the second and third piezoelectric parts 1000*b* and 1000*c* may be provided to the first piezoelectric part 1000*a* corresponding to the brow region that is relatively insensitive to stimulation. That is, the first piezoelectric part 1000*a* may provide ultrasonic energy stronger than those of the second and third piezoelectric parts 1000*b* and 1000*c* to the user's skin.

Therefore, the skin care device 1 may effectively care and treat by providing optimal ultrasound energy according to the user's skin region, and may prevent stimulation by applying a relatively strong ultrasound to the skin region sensitive to stimulation.

The characteristics, structures, effects, and the like described in the above-described embodiments are included in at least one embodiment of the present invention, but are not limited to only one embodiment. Furthermore, the characteristic, structure, and effect illustrated in each embodiment may be combined or modified for other embodiments by a person skilled in the art. Therefore, it should be construed that the contents related to such combination and modification are included in the scope of the present invention.

In addition, the above description has been focused on the embodiments, but it is merely illustrative and does not limit the present invention. Those skilled in the art to which the embodiments pertain may appreciate that various modifications and applications not illustrated above are possible without departing from the essential features of the embodiment. For example, each component particularly represented in the embodiments may be modified and realized. In addition, it should be construed that differences related to such a modification and an application are included in the scope of the present invention defined in the appended claims.

The invention claimed is:

1. A mask comprising:

a body having a shape corresponding to a user's face;

a first recess disposed on one surface of the body; and a piezoelectric part disposed in the first recess, wherein the first recess has a concave shape from one surface of the body in an outward direction and is disposed in a region corresponding to at least one of the user's brow region and eye rim regions, wherein the piezoelectric part protrudes further toward the user than one surface of the body, wherein the body includes:

a first support member;

a second support member disposed below the first support member; and a third support member disposed between the first and second support members, wherein the third support member includes a material different from that of the first and second support members, wherein the piezoelectric part has a shape corresponding to the first recess, wherein the first recess is formed on the first support member and exposes an upper surface of the third support member, wherein the mask further comprises a second recess disposed in the first recess and formed on the third support member, and wherein the second recess exposes an upper surface of the second support member.

2. The mask of claim 1, wherein the first recess is formed on the first and third support members and exposes an upper surface of the second support member.

3. The mask of claim 1, wherein the second recess is disposed in a region corresponding to a piezoelectric element of the piezoelectric part in a vertical direction, and wherein a width of the second recess in the horizontal direction is 40% to 160% of a width of the piezoelectric element in the horizontal direction.

4. The mask of claim 1, comprising an adhesive member disposed between the body and the piezoelectric part.

5. The mask of claim 1, wherein the piezoelectric part comprises:

a first base layer disposed on the second support member;

a first wiring disposed on the first base layer;

a plurality of piezoelectric elements disposed on the first wiring;

a second wiring disposed on the plurality of piezoelectric elements;

a second base layer disposed on the second wiring; and a protective layer disposed between the first and second base layers and surrounding the first wiring, the second wiring, and the plurality of piezoelectric elements.

6. The mask of claim 5, wherein the first base layer, the second base layer, and the protective layer include the same material.

7. The mask of claim 6, wherein at least one of the first and second support members includes the same material as those of the first base layer, the second base layer, and the protective layer.

8. The mask of claim 1, wherein the first and second support members includes at least one of silicone, a thermoplastic resin, a thermoplastic silicone resin, a thermoplastic elastomer, a polyurethane elastomer, ethylene vinyl acetate (EVA), a polyvinyl chloride (PVC) material in which a harmless plasticizer and a stabilizer are added.

9. The mask of claim 8, wherein the first and second support members are provided transparent or colored.

10. The mask of claim 8, wherein the third support member includes at least one metal of aluminum (Al), copper (Cu), silver (Ag), gold (Au), platinum (Pt), chromium (Cr), nickel (Ni), molybdenum (Mo), and titanium (Ti), tin (Sn), tungsten (W), iron (Fe), and alloys thereof.

11. The mask of claim 1, wherein the body includes:

an opening formed in a region corresponding to the user's eyes;

a bending portion formed in a region corresponding to the user's nose;

an extension portion extending from at least one end of the body and connected to the other end of the body; and a fixing member disposed on the extension portion and fixing the extension portion.

12. A mask comprising:

a body having a second support member, a third support member on the second support member, and a first support member on the third support member;

a first recess disposed on the first support member; and a piezoelectric part disposed in the first recess, wherein the first recess has a concave shape from the first support member toward the second support member, wherein the third support member includes a material different from that of the first and second support members, wherein the piezoelectric part includes:

a first base layer disposed on the second support member;

a first wiring disposed on the first base layer;

a plurality of piezoelectric elements disposed on the first wiring;

a second wiring disposed on the plurality of piezoelectric elements;

a second base layer disposed on the second wiring; and a protective layer disposed between the first and second base layers and surrounding the first wiring, the second wiring, and the plurality of piezoelectric elements, wherein an upper surface of the second base layer is disposed above an upper surface of the first support member, wherein the mask further comprises a second recess disposed in the first recess and formed on the third support member, and wherein the second recess exposes an upper surface of the second support member.

13. The mask of claim 12, wherein the piezoelectric part has a shape corresponding to the first recess, and wherein the first recess is formed on the first and third support members and exposes an upper surface of the second support member.

14. The mask of claim 12, wherein the first recess is formed on the first and third support members and exposes the upper surface of the second support member.

15. The mask of claim 12, wherein the first base layer, the second base layer, and the protective layer include the same material.

16. The mask of claim 15, wherein at least one of the first and second support members includes the same material as those of the first base layer, the second base layer, and the protective layer.

* * * * *